(12) United States Patent
Ehrenfeld Stolzenbach et al.

(10) Patent No.: US 8,207,324 B2
(45) Date of Patent: Jun. 26, 2012

(54) ARRAY OF NUCLEOTIDIC SEQUENCES FOR THE DETECTION AND IDENTIFICATION OF GENES THAT CODIFY PROTEINS WITH ACTIVITIES RELEVANT IN BIOTECHNOLOGY PRESENT IN A MICROBIOLOGICAL SAMPLE, AND METHOD FOR USING THIS ARRAY

(75) Inventors: Katia Nicole Ehrenfeld Stolzenbach, Los Condes (CL); Juan Ugalde, Ñuñoa (CL); Andrés Octavio Aravena Duarte, Nuñoa (CL); Nicolas Loira, Las Condes (CL); Alejandro Eduardo Maass Sepúlveda, Peñlolén (CL); Pilar A. Parada Valdecantos, Nuñoa (CL); Ricardo Badilla Ohlbaum, La Reina (CL)

(73) Assignee: Biosigma S.A., Colina (CL)

( * ) Notice: Subject to any disclaimer, the term of this patent is extended or adjusted under 35 U.S.C. 154(b) by 235 days.

(21) Appl. No.: 12/048,027

(22) Filed: Mar. 13, 2008

(65) Prior Publication Data
US 2009/0105085 A1    Apr. 23, 2009

(30) Foreign Application Priority Data
Mar. 13, 2007   (CL) .................................... 660-2007

(51) Int. Cl.
  *C07H 21/04*   (2006.01)
  *C07H 21/02*   (2006.01)
  *C12Q 1/68*    (2006.01)
  *C40B 30/04*   (2006.01)
  *C40B 40/08*   (2006.01)
  *C40B 50/00*   (2006.01)

(52) U.S. Cl. .............. 536/24.32; 435/6.1; 435/6.11; 435/6.15; 506/9; 506/17; 536/23.1; 536/23.7

(58) Field of Classification Search .............. 435/6.1, 435/6.11, 6.15; 506/9, 17; 536/23.1, 23.7, 536/24.32
See application file for complete search history.

(56) References Cited

U.S. PATENT DOCUMENTS
2002/0187476 A1* 12/2002 Koroulis et al. .................. 435/6

FOREIGN PATENT DOCUMENTS
WO    WO 2004/092409    * 10/2004

OTHER PUBLICATIONS

Richmond et al. (Genome-wide expression profiling in *Escherichia coli* K-12, 1999, Nucleic Acids Research, vol. 27, pp. 3821-3835).*
Tiquia et al. (Evaluation of 50-mer oligonucleotide arrays for detecting microbial populations in environmental samples, 2004, BioTechniques, vol. 36, pp. 664-668, 670, 672, 674-675).*

(Continued)

*Primary Examiner* — Amber D Steele
*Assistant Examiner* — Shannon Janssen
(74) *Attorney, Agent, or Firm* — Merchant & Gould P.C.

(57) ABSTRACT

The present invention makes known an array of nucleotidic sequences for rapidly and simultaneously identifying the presence of certain genes that codify proteins with relevant activities in biotechnology present in a microbiological sample, and the method with which this array is used in the identification of the above mentioned genes. Specifically speaking, genes that codify for proteins relevant in the biofilm formation, in $CO_2$ fixation, in energetic metabolism, for chemiotaxis and mobility, in iron oxidizing, in nitrogen metabolism, in sulfur assimilation, and in oxidation/reduction of sulphide compounds, are identified. This array of nucleotidic sequences is presented as a useful tool in biotechnology whenever evaluating the quality of a microbiological community is required.

5 Claims, 1 Drawing Sheet

OTHER PUBLICATIONS

Schena et al. "Microarrays: biotechnology's discovery platform for functional genomics." *TIBTECH*. vol. 16. 1998. pp. 301-306.

Ye et al. "Applications of DNA microarrays in microbial systems." *Journal of Microbiological Methods*. vol. 47. 2001. pp. 257-272.

* cited by examiner

ARRAY OF NUCLEOTIDIC SEQUENCES FOR THE DETECTION AND IDENTIFICATION OF GENES THAT CODIFY PROTEINS WITH ACTIVITIES RELEVANT IN BIOTECHNOLOGY PRESENT IN A MICROBIOLOGICAL SAMPLE, AND METHOD FOR USING THIS ARRAY

SCOPE OF THE INVENTION

The present invention makes known an array of nucleotidic sequences for rapidly and simultaneously identifying the presence of certain genes that codify proteins with relevant activities in biotechnology present in a microbiological sample, and the method with which this array is used in the identification of the above mentioned genes. Specifically speaking, genes that codify for proteins relevant in the biofilm formation, in $CO_2$ fixation, in energetic metabolism, for chemiotaxis and mobility, in iron oxidizing, in nitrogen metabolism, in sulphur assimilation, and in oxidation/reduction of sulphide compounds, are identified. This array of nucleotidic sequences is presented as a useful tool in biotechnology whenever evaluating the quality of a microbiological community is required.

BACKGROUND OF THE INVENTION

Biotechnology is, generally speaking, any technological application that uses biological systems (such as a complex microbiological community), living organisms (microorganisms, animals or plants) or their derivates (metabolites, proteins, nucleic acids) in the creation or modification of products or processes for specific uses. In this invention, we will focus on the biotechnology that employs microorganisms, especially biomining and microbiological bioremediation.

Many processes of microbiological biotechnology are carried out strengthening the development of the microbiological community originally present in the substrate to be treated, for instance the community present in ore in the case of biomining, or present in contaminated soil or water in the case of bioremediation. In these cases having a tool that that would allow us to evaluate the metabolic characteristics of the community present, would be of great use, for example, in judging whether the process we are interested in can be carried out with the community present, or if we should inoculate other adequate strains.

Up to now, the most common approach used in evaluating microbiological communities has been the identification of species present, by means of a variety of techniques such as selective cultures, fluorescent in situ hybridization (FISH), conjugated with specific markers such as detection probes, polymerase chain reaction (PCR) and macro and micro DNA arrays. Among the previously mentioned techniques, all the ones pertaining to molecular biology, that is to say FISH, detection probes, PCR, and macro and micro DNA arrays, are based on hybridizing the DNA of the unknown sample with known sequences that are specific for the microorganism or microorganisms that need to be detected or identified, for example, a certain specie or genus.

The problem with the previous approach is that there are many types of different microorganisms that may be present in these microbiological communities, so that many tests should be carried out to establish their composition, and then correlate these acquired data with the characteristics of each identified taxon, to finally establish whether the function of interest is present in the sample. If there were a microorganism not previously described, this correlation could not be carried out, even if it's metabolic activities were known, and even important for the process. So it rises the need for a method oriented for directly evaluating and controlling the metabolic characteristics of a microbiological community, and not for identifying what microorganisms it is composed of.

This technical problem has been resolved by means of the present invention, by creating an array of nucleotidic sequences for detecting and identifying genes that codify proteins with relevant activities in biotechnology present in a microbiological sample, and a Method for employing this array.

When changing the focus of the approach from the taxonomy of the studied community to the identification of proteins with relevant activities present in this community, we focus directly on the essential of the biotechnological process: the metabolic functions which ultimately carry out these processes. For example, each time the presence of *Leptospirillum* spp. is sought for in a bioleaching process, what really is being sought for is iron oxidization, and it is so for each of the microorganisms that are relevant in some biotechnological process.

The new approach, designed by us, makes it possible to respond to exactly what the operator of a biotechnological process requires: Does this community oxidize iron?, does it oxidize sulfur?, does it fix $CO_2$?, does it fix nitrogen? With the approach that currently exists in the technique, the operator first knows what species are present, and then he or she must correlate this information with the characteristics of each of these species in order to answer the same questions.

In each case, we have designed fragments of DNA for identifying the genes that codify proteins with relevant activities in biotechnology that comply with an essential condition: the specificity of the mentioned fragment must correspond solely to the target gene. On the other hand, whenever it has been possible, regions have been sought which being specific for each target gene, and orthologically conserved. This is with the idea of detecting not only the genes that have been sequenced, but also genes that have not been described, that are orthologues of each target gene. The result of this search corresponds to fragments that are specific for a certain gene or function within a specific taxon in a specific region.

With these DNA fragments designed we have developed DNA fragment arrays which allow us to carry out the identification of the presence of these genes that codify proteins with relevant activities in biotechnology, which are present in a microbiological sample.

A good definition of DNA arrays is the one proposed by Schena and colleagues: "a microscopic and methodical arrangement of nucleic acids that allow simultaneous analysis of complex DNA samples" (Schena M., Heller, R. A., Theriault, P., Konrad, K., Lachenmeier, E. and Davis, R. W. Trends Biotechnol. 16, 301-306, 1998). Depending on the diameter of the printed DNA dot there are 2 types of arrays, macro arrays (300 microns or more), and micro arrays (less than 100 microns). The former can be made manually in the laboratory and the dots can be visualized without the help of special equipment. The latter require an automated printing system (normally a robotic printing platform) and specialized acquisition and image-processing equipment.

In the present invention, DNA fragment arrays include an ordered series of dots printed on a flat surface such as a sheet of glass, silicone or nylon, where each dot contains a large quantity of copies of a DNA fragment that is known and specific for a certain gene of interest in biotechnology.

The detection method that employs DNA fragment arrays includes simultaneous hybridization of the set of 'dots' of the array with an extract of labeled DNA from the sample under study. Normally, the DNA of the sample which has been labeled and in given case fragmented, is submitted to a denaturing stage in which the double strand of DNA separates, for example, with heat. As the temperature is lowered, the DNA, due to its physical-chemical characteristics, will tend to hybridize with its most exact complementary. When this DNA is in contact with the array, if there is a coincidence between the DNA of the sample and the fragment of DNA contained in the dot, the copies of the sample's labeled DNA will most probably remain linked specifically to that dot. This occurs due to the higher number of copies of complementary DNA contained in the dot of the array. In the image acquisition and processing stage of the hybridized array, this label will allow the detection of microorganisms present in the sample under study.

DNA labeling can be done with any known labeling technique, the most common of which are fluorescent or radioactive label.

The arrays and their use are known, and in the state of the art we find examples of arrays that detect the presence of microorganisms in a sample, but none of them focus on the detection of genes that codify proteins with relevant activities in biotechnology.

There are currently various protocols published for manufacturing DNA fragment arrays, as well as laboratories that render services in the manufacture of this kind of arrays. As a result, only the selection of the genes and the design of the fragments of DNA used, is what defines the specificity and usefulness of an array, because manufacture may vary in regard to the support, the method with which the fragments of DNA are bound to the support, the spatial distribution of the dots on this support, etc., depending on the company entrusted with the array manufacturing or the protocol employed for doing it in the laboratory itself. (Ye et al Journal of Microbiological Methods 47 (2001) 257-272).

SUMMARY OF THE INVENTION

The present invention makes known an array for rapidly and simultaneously identifying the presence of certain genes that codify proteins with relevant activities in biotechnology that are present in a microbiological sample, and the method for using this array in the identification of said genes.

We have designed DNA fragments 100 or less nitrogenated bases long, that make it possible to identify the presence of genes that codify for proteins relevant in biofilm formation, in $CO_2$ fixation, in energetic metabolism, in chemiotaxis and mobility, in iron oxidization, in nitrogen metabolism, in sulfur assimilation, and in oxide-reduction of sulfide compounds. All the designed fragments are specific for genes that codify particular proteins, which are related to the function of interest, and therefore we say they are specific for certain metabolic functions. In some cases, the genes based on which the oligonucleotides have been designed are specific for only one specie, and consequently, the oligonucleotide is specific both for the function and the specie. In other cases, the genes of interest are found orthologically conserved. In these cases the oligonucleotides were designed within the region of consensus among the described orthologues, and are thus specific for the function and taxon under discussion.

When there is at least one of these fragments of DNA in an array, it is possible to evaluate the metabolic characteristics of a microbiological community. Arrays containing several of the designed DNA fragments that make it possible to identify simultaneously and in only one process the presence of several or all of the genes that codify for proteins relevant in biofilm formation, in $CO_2$ fixation, in energetic metabolism, in chemiotaxis, in nitrogen metabolism, in sulfur assimilation and in oxide-reduction of sulfide compounds, are preferably provided.

This method is presented as a tool that is useful in biotechnology whenever evaluating or controlling the qualities of a microbiological community regarding its specific metabolic functions is required.

DETAILED DESCRIPTION OF THE PREFERRED EMBODIMENTS

Figure 1:
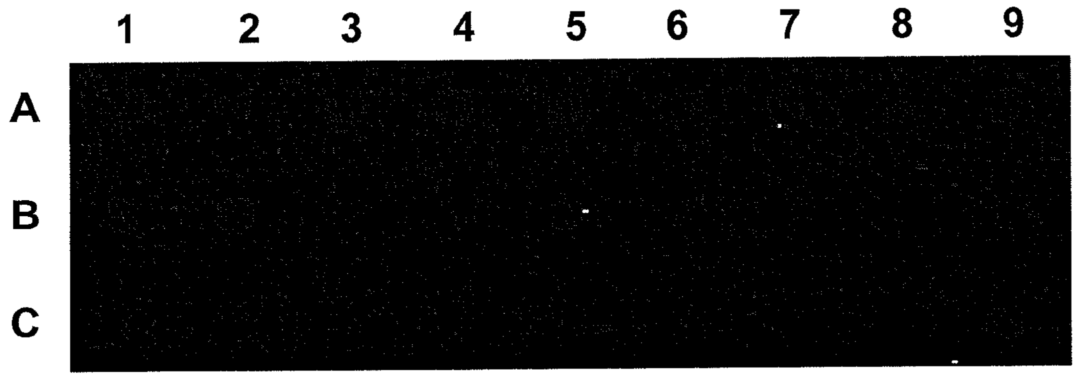
FIG. 1 corresponds to the result of hybridization of biomining sample 1 with a microarray of the invention. The fragments of the invention correspond to subfragments of the fragments described in Table 2. In Table 1, the contents of each of the positions of the microarray are detailed, and Table 3 sums up the positive or negative results of the hybridization. The results show the presence of genes that codify for proteins relevant in the following functions: metabolism of sulfide compounds, $CO_2$ fixation, iron oxidizing, nitrogen fixation, and in key enzymes of energetic metabolism. The sample doesn't seem to have the genes evaluated for chemiotaxis and biofilm formation. Positive controls showed signs of hybridization, and negative controls remained unlabeled.

Being provided with an array that allows rapid and simultaneous detection of the presence of genes that codify proteins with activities relevant in biotechnology that are present in a microbiological sample would have applications in various areas of industrial business, and the method for using this array. For example, evaluation of wild microbiological communities present in biotechnological process substrates, such as minerals, for biomining processes; contaminated soils or water, for bioremediation processes, or any other of biotechnological application. A second aspect is that it would also allow microbiological communities already involves in a biotechnological process to be controlled.

In order to fulfill these biotechnological industrial business needs we have designed DNA fragments 100 or less hydrogenated bases long, that are specific for genes that codify for proteins relevant in biofilm formation, in $CO_2$ fixation, in energetic metabolism, in chemiotaxis and mobility, in iron oxidization, in nitrogen metabolism, in sulfur assimilation, and in oxidation-reduction of sulfide compounds. These fragments, distributed in DNA arrays, make it possible to identify the presence of these genes in a sample obtained from a microbiological community, whether wild, or already involved in a biotechnological process.

All the fragments designed are specific for genes that codify specific proteins related to the function of interest and thus, we say they are specific for certain metabolic functions, specifically for the following functions: biofilm formation, $CO_2$ fixation, energetic metabolism, chemiotaxis and mobility, iron oxidization, nitrogen metabolism, sulfur assimilation, and oxide reduction of sulfide compounds.

In some cases, the genes based on which the oligonucleotides have been designed are specific for only one specie, and consequently, the oligonucleotide is specific both for the function and the specie. In other cases, the genes of interest are orthologically conserved in different species within a specific genus. In these cases, the oligonucleotides were designed within the region of consensus between the described orthologues, and are thus specific for the function and for the taxon under discussion.

For a better understanding of how we developed this method, we will briefly describe the strategy employed.

In the first place, we established the functions of interest in biotechnology we wanted to detect, and the key genes for each of these functions.

In the second place, microorganisms with genes related to the functions of interest which should comply with two basic conditions, on one hand to possess any of the functions of interest, and on the other, to be completely or partially sequenced, were chosen.

In the third place, a list of reference sequences that codify for the protein or function of interest in well known microorganisms, as for example in *E. coli* was generated, and homology between the said known genes and the genomes of interest was inspected. In the cases in which homology was found, it was defined that the 'homologous' zone corresponds to the gene of interest in the microorganism of interest.

A start-up data base containing the sequence of each of the genes of interest in each of the microorganisms of interest was obtained this way. Obviously, not all the genes of interest were present in all the microorganisms of interest (this is a known microorganism/sequenced genome).

The sequences of the genes contained in the start-up data base were compared with all the genes of the microorganisms of interest, selecting only the regions that are specific for the genes of interest, in other words, the regions that do not exhibit homology with genes that have other functions. This selection is made by a search algorism into which these restrictions are entered.

The specific regions thus selected are grouped together by high similarity, which is understood as a coincidence of about 80% of the final length of the designed oligonucleotide, with the purpose of detecting possible consensus regions.

These specific regions are validated as regions useful for detection, taking physical-chemical variables of the oligonucleotides (GC composition level, hybridization temperature, possible secondary structures) into consideration. The regions that comply with these conditions are considered to be oligonucleotide candidates.

The oligonucleotide candidates are compared by homology with all the known gene sequences, excluding from this comparison the gene of interest based on which the oligonucleotide was designed with which there would obviously be homology.

The oligonucleotides adopted as specific, are the ones we will employ to detect the function of interest.

As it was previously indicated, the first step was to select the functions of interest. We selected 8 of the metabolic functions that exist in a microbiological community and are useful in biotechnology to include in our DNA array: biofilm formation, $CO_2$ fixation, energetic metabolism, chemiotaxis and mobility, iron oxidization, nitrogen metabolism, sulfur assimilation, and oxide reduction of sulfide compounds. The importance of each of them is evident for any person with thorough knowledge of the technique.

Some of these functions provide us with general and relevant information on any microbiological community, for example, both energetic metabolism and whether the community can or cannot fix $CO_2$ or nitrogen, are relevant in establishing the nutrients a community needs. Knowing the community's biofilm-formation capability, or the presence of microorganisms capable of moving within the community, is likewise essential in establishing the culture conditions of the biotechnological process that we want to carry out. In another direction, iron oxidization, sulfur assimilation, and sulfide compound oxidation/reduction processes are important processes in specific biotechnological processes of great importance, such as biomining and bioremediation.

In the second place, the microorganisms of interest based on which the oligonucleotides that will be included in the microarray were designed, were determined. The selection was carried out keeping two relevant aspects in mind: first that the microorganisms possess at least one of the functions of interest, and second, that their genome be totally or partially sequenced. Considering these factors, the strains that are property of Biosigma: Wenelen (DSM 16786) and Licanantay (DSM 17318), and possess one or more of the mentioned metabolic functions and for which there is a sequenced genome, were selected. The *Acidithiobacillus ferrooxidans* ATCC 23270 species which possesses iron and sulfide compound oxidizing functions was also included. The *Burkholderia pseudomallei* species for which two published sequences were used: *Burkholderia pseudomallei* 1710b and *Burkholderia pseudomallei* K96243. *Desulfovibrio desulfuricans* was selected for the sulfur-oxidizing activity, and the published *Desulfovibrio desulfuricans* G20 series was used; *Thiobacillus denitrificans* ATCC 25259, whose function is sulfide compound oxidization, was also included. Biomining microorganisms *Ferroplasma, Leptospirillum, Sulfolobus* and *Thermoplasma*, in which the published sequences correspond to the following microorganisms; *Ferroplasma acidarmanus, Ferroplasma* sp. (II), *Leptospirillum* sp. (II), *Leptospirillum* sp. (III) *Sulfolobus acidocaldarius* DSM 639, *Sulfolobus solfataricus, Sulfolobus tokodaii, Thermoplasma acidophilum* and *Thermoplasma volcanium*, were also included.

Once it is clear which the functions of interest and the microorganisms with which we will work are, we determine what genes we will employ to identify the presence of the said function. A brief description of each of the functions of interest and the genes chosen to represent them is presented below.

Description of Functions of Interest

Iron oxidization. Iron oxidization from $Fe^{+2}$ to $Fe^{+3}$, is fundamental for the development of bioleaching, because the iron (III) generated is a great oxidizing agent, which can oxidize the sulfides present or any compound that requires oxidizing, thus releasing the metals of interest into the solution.

In order to identify the presence of the 'iron oxidization' function, the following genes codifying for proteins that are relevant within the process, based on *A. ferrooxidan*, were chosen:

rus, cyc1, cyc2, cycA y cycA2

Definition of the sequences for all these genes within the microorganisms of interest (known microorganisms/sequenced genome) was available, on account of which it was not necessary to employ reference sequences.

Biofilm formation. The capacity to form biofilm or silt, is important for the development of any bacterial community, because it assures permanence of the biomass attached to a support.

In order to identify the presence of the 'biofilm formation' function, the following genes that codify for proteins relevant within the process were chosen.

galE, galU, rfbA, rfbB, rfbC, rfbD, epsD, gdh, manB, manC, pgm, uppS, wza, wzc

There was no information available on these genes in the microorganisms of interest, so work was done with reference genes looking for homology between the said genes and the genomes of the microorganisms of interest, to determine the 'probable' presence of these genes. In most cases, the gene of *E. Coli* was used as reference, except with epsD, in which the gene of *Lactobacillus lactis* was used as reference.

$CO_2$ fixation. $CO_2$ fixation is important in microbiological biotechnological processes because it allows evaluating whether the community is autotrophous, which grants economic advantages to the process, because it is not necessary to add carbonated substrates to the community.

In order to identify the presence of the '$CO_2$-fixation' function, the following genes that codify for proteins relevant within the process were chosen:

cbbL1, cbbL2, cbbM, cbbS1, cbbS2, cbbArchea, ppc, prk

Information for only some of these genes in the microorganisms of interest, cbbL1, cbbL2, cbbM, cbbS1 and cbbS2 was available. In the other cases, work was done with reference genes, and homology between these reference genes and the genomes of the microorganisms of interest was sought in order to determine the 'probable' presence of these genes. For gene cbb of Archaeas, *Methanosarcina acetivorans* was used as reference, for gene ppc, the gene of *E. coli* was used as reference, and for gene prk, the gene of *Synechococcus* was used.

Chemiotaxis and mobility. Microorganism mobility is given by the presence of flagellums; in given cases, movement develops as a response to the concentration of a metabolite in the medium, which is known as chemiotaxis. Knowing whether a microbiological community has the characteristics of chemiotaxis and mobility makes it possible to establish in a better way the culture conditions for the biotechnological process to be developed.

In order to identify the presence of the 'chemiotaxis and mobility' function, the following genes that codify for proteins relevant in the process were chosen:

flhA, flhB, fliF, fliG, fliM, fliN, motA, motB

No information on any of these genes in the microorganisms of interest was available, so work was done with reference genes, and homology between these reference genes and the genomes of the microorganisms of interest was sought in order to determine the 'probable' presence of the said genes. In every case, the gene of *E. coli* was used as reference.

Nitrogen metabolism. Regarding the metabolism of nitrogenated compounds, there are two processes which can be considered to be important. One of them is nitrogen fixation in which the essential component is the enzyme nitrogenase. The other is the degradation of nitrogenated compounds, in which nitrate reductases participate.

In order to identify the presence of the 'nitrogen metabolism' function, the following genes that codify for proteins relevant within the process were chosen:

nifK, narH, nirA

No information on these genes in the microorganisms of interest was available, so work was done with reference genes, and homology between these reference genes and the genomes of the microorganisms of interest was sought in order to determine the 'possible' presence of these genes. In the case of narH, the gene of *E. coli*; was used as reference; for nifK, *Azotobacter vinelandii* was used as reference, and in the case of nirA, the reference was *Synechococcus.*

Sulfur assimilation. Sulfur assimilation is the process through which environmental sulfur is fixed as organic sulfur for its use in cell metabolism. The two main final products of this process are the essential amino acids cysteine and methionine.

In order to identify the presence of the 'sulfur assimilation' function, the following genes that codify for proteins relevant within the process were chosen:

cysI, cysJ

No information on these genes in the microorganisms of interest was available, so work was done with reference genes, and homology between these reference genes and the genomes of the microorganisms of interest was sought in order to determine the 'probable' presence of the said genes. For genes cysI, and cysJ, the gene of *E. coli* was used as reference.

Oxidation/reduction of sulfide compounds. A highly relevant process in bioleaching is the oxidization of sulfur compounds. For example, microorganisms of the *Acidithiobacillus* genus are capable of catalyzing the oxidization of reduced sulfur compounds (such as sulfide, elemental sulfur, thionates, etc.) using oxygen as an electronic acceptor and generating sulfuric acid as a final product, and reducing species such as sulfite and thiosulfate as intermediate products which makes solubilization of the metal associated to sulfides in the ore possible.

In order to identify the presence of the 'sulfur oxidization' function, the following genes that codify for proteins relevant within the process were chosen:

doxA, doxD, doxDA1, doxDA2, dsrA, dsrB, dsrC, dsrE, dsrF, dsrK, dsrL, dsrM, dsrN, dsrO, dsrP, dsrS, soxB There was only information available for the doxDA1, doxDA2 genes in the microorganisms of interest. In other cases, work was done with reference genes, and homology between these reference genes and the genomes of the microorganisms of interest was sought in order to determine the 'probable' presence of these genes. For genes doxA, doxD, *Acidarmanus Ambivalens* was used as reference; for gene soxB, the gene of *Paracoccus denitrificans* was used as reference, and for all the dsr genes, genes of *Allochromatium vinosum* were used.

Energetic Metabolism.

In order to identify the presence of the 'energetic metabolism' function, the following genes that codify for proteins relevant within the process were chosen:

pfk, korA, korB, idh, pdhA, pdhB, pdhC, gltA, accA, accB, aaC, accD

There was only information available for the pdhC gene in the microorganisms of interest. In other cases, work was done with reference genes, and homology between these reference genes and the genomes of the microorganisms of interest was sought in order to determine the 'probable' presence of these genes. For genes pfk, idh, gltA, accA, accB, aaC and accD, the gene of *E. coli* was used as reference. For genes korA and korB, *Methanocaldococcus jannaschii* was used as reference and for genes pdhA and pdhB, the genes of *Mycobacterium tuberculosis* were used.

The published array of nucleotidic sequences for detecting and identifying genes that codify previously defined proteins with relevant activities in biotechnology present in a microbiological sample includes, adhered to its surface, a representative of one, several, or all of the following fragments of DNA:

a. at least one fragment of DNA that specifically identifies a gene that codifies for a protein relevant in biofilm formation;

b. at least one fragment of DNA that specifically identifies a gene that codifies for a protein relevant in the $CO_2$-fixation process;

c. at least one fragment of DNA that specifically identifies a gene that codifies for a protein relevant in energetic metabolism;

d. at least one fragment of DNA that specifically identifies a gene that codifies a protein relevant for chemiotaxis and mobility;

e. at least one fragment of DNA that specifically identifies a gene that codifies for a protein relevant in iron oxidization;

f. at least one fragment of DNA that specifically identifies a gene that codifies for a protein relevant in nitrogen metabolism;

g. at least one fragment of DNA that specifically identifies a gene that codifies for a protein relevant in sulfur assimilation;

h. at least one fragment of DNA that specifically identifies a gene that codifies for a protein relevant in oxidation/reduction of sulfide compounds;

where each fragment of DNA is present in hundreds of copies, forming dots of homogeneous composition, spatially distributed over the surface of the support.

For each of these previously mentioned genes we have designed fragments of 80 to 100 specific nitrogenated bases, preferably 100 specific nitrogenated bases, which are made known in the list of sequences.

In all, we designed a total of 232 fragments of DNA for identification of genes that codify proteins with relevant activities in biotechnology, all of which are 100 nucleotides long. The sequences of the 232 DNA fragments designed are included in the listing of sequences.

Out of the 232 sequences designed, sequences No 1 to 86 are specific for the biofilm formation function.

Sequences 87 to 101 are specific for the $CO_2$-fixation function.

Sequences 102 to 156 are specific for the energetic metabolism function.

Sequences 157 to 192 are specific for the chemiotaxis and mobility function.

Sequences No 193 to 197 are specific for the iron oxidization function.

Sequences No 198 to 203 are specific for the nitrogen metabolism function.

Sequences No 204 to 210 are specific for the sulfur assimilation function.

And sequences 211 to 232 are specific for the sulfide compound oxide reduction function.

The fragments designed can be imprinted in the array, whether complete or in a larger fragment that includes it, or partially like any of the subfragments included in the fragment, or as the reverse complement sequences of all the previous options. Subfragments of 50 to 70 nucleotides are conveniently imprinted.

It is necessary to keep in mind that the arrays contained in the present invention are those that comprise at least one of the DNA fragments included in sequences No 1 to 232, whether completely; in a larger region in which the said fragment represents over 20% of the region, just like a PCR product; or partially, as one of the subfragments contained in each of the fragments published here, or as the reverse complement sequences of all the previous options.

The previous aspect is of vital importance, because the specificity of a nucleotidic sequence is the same as that of its reverse complement sequence. It is this characteristic, specificity, which is the hardest to attain in the design of DNA fragments. It could happen that the stability of the complement sequence is not appropriate for use in an array, although a person with thorough knowledge of the technique could distinguish between thermodynamically stable and non-stable oligonucleotides using a series of tools that exist in the technique. All the reverse complement sequences of fragments No 1 to 232 of the present invention, whether completely; in a larger region that contains it, such as a PCR product; or partially, as one of the subfragments contained in each of the fragments published here, are considered to be within the scope of the present invention.

The array will preferentially contain at least one fragment or subfragment for each fragment of interest. It is also possible to prepare an array containing all the published fragments or subfragments of DNA, or in a given case, only one of them. All these options, as well as all the possible intermediate combinations, are included in the scope of the present invention.

Effectiveness of the arrays of the invention is given by the specificity and stability of the fragments to be imprinted. These characteristics persist in each of the subfragments contained in the designed fragments. This means that specificity keeps the same if nucleotides 1 to 100, or 42 to 92 or 15 to 65 or any other possible selection is used. Every selection corresponds to subfragments and is included in the scope of the present invention.

It is also possible to obtain DNA fragments that contain the fragments or subfragments of the present invention flanked by other oligonucleotides, whether through synthesis or as products of PCR. These larger regions that contain the fragments of the present publication, in which specificity is given by the fragments or subfragments designed and made known in the present invention, are also found contained in the scope of the present invention.

In order to carry out an array according to the invention, each fragment or subfragment selected must be synthesized, in several hundreds of copies, and imprinted, like a homogeneous dot, on a support appropriate for an array, such as glass, silicone, nylon, or any other that exists in the technique.

Just as we indicated when discussing the background information for this invention, DNA fragment synthesis and array-making techniques are known, and any of them can be used in making the arrays of the present invention.

Added to these specific DNA fragments for genes that codify proteins with relevant activities in biotechnology, it is convenient to include negative and positive controls in each array. Negative controls should correspond to nucleotidic sequences that should never be found in a biotechnological context. Positive controls should correspond to nucleotidic sequences that are always present in the problem sample.

For an expert in the technique, it will be obvious that the 232 fragments of DNA designed for the present invention allow identification of genes that codify proteins with relevant activities in biotechnology, not only when used in an array but also in other molecular biology techniques based on the hybridization of an unknown DNA with a specific fragment. Among these molecular biology techniques we can mention detection probes, FISH, PCR and sequencing, for example.

Using the 232 fragments of DNA made known in this invention, whether completely; in a larger region in which the said fragment represents over 20% of the region, just like a product of PCR; or partially, as one of the subfragments contained in each of the fragments made known here; or as reverse complement sequences of all the previous options, in any molecular biology technique it is considered an obvious application of the present publication and within the scope of the present invention.

Use of the Array

In order to detect and identify the presence of certain genes that codify proteins with relevant activities in biotechnology present in a microbiological sample using the arrays of the present invention, in the first place it is necessary to isolate the DNA of the sample we are interested in evaluating. It is also possible to work with cDNA where the only difference is that in this case the RNA of the sample is isolated in the first stage. In the technique, different methods for extracting DNA and RNA from environmental samples or from cultures are known, and any of them can be used, considering in each case the particular nature of the sample.

During a second stage, all the DNA or RNA of the sample must be converted to short fragments of labeled DNA which are appropriate for hybridizing with the fragment imprinted in the dots of the array. If the DNA of the sample has been isolated, it must be fragmented and labeled. When not working with the RNA of the sample, it is not necessary to fragment and the marking stage should only be carried out to obtain labeled cDNA. A technique that allows both fragmentation and marking of the DNA is marking with aleatory splitters of 6 nucleotides of DNA. Marking can be done employing nucleotides that are labeled or susceptible to being labeled with any of the existing techniques of the art, such as radioactivity, biotine, fluorescence, or others. If a macroarray is to be uses, marking should be preferably done with radioactivity, $^{32}P$, and if a microarray is to be used, it will be with fluorescence, for example, with Cy5 or Cy3.

The methods described for the preparation of DNA or cDNA for the array, are not limiting for the present invention, and any method existing in the state of the art for the preparation of DNA or cDNA can be used, which doesn't mean that the use of the array can break away from the scope of the present invention.

Once the DNA is prepared, it is submitted to a DNA denaturing stage. This denaturalized DNA is then incubated on the array, placing an aliquot of the DNA mixture on the array. The array is left to hybridize at a temperature within the range of 40 to 70° C. for at least an hour and preferably all night.

After hybridization, the array should be carefully washed. Washing is usually done with softening solutions at moderate temperatures, for example from 35-50° C., and preferably from 40-45° C.

Once the array is washed, it is preferentially dried, conveniently by centrifugation, for example, in a Falcon tube or something similar, for a short time and at a moderate speed (200-3000×g per 1 to 5 minutes).

Finally, it is necessary to visualize which dots exhibit marking. The position of each labeled dot indicates the presence of the gene that codifies a protein with relevant activity in biotechnology based on which the fragment of DNA was designed.

It is necessary to check that the dot or dots corresponding to the negative control remain unlabeled, because if there is hybridization with these fragments of DNA, this indicates that the reaction was unspecific and that the results obtained must be discarded because they could contain false positives.

The dots corresponding to the positive control should likewise be labeled, because when no hybridization with this fragment of DNA takes place, this indicates that there was interference in the reaction and that therefore the dots with no signs can correspond to false negatives.

According to the above, determining the presence of certain genes that codify proteins with relevant activities in biotechnology in a microbiological community would be reduced to the reading of the labeled dots in an array of the present invention.

EXAMPLES

Example 1

Microarray to Detect and Identify the Presence of Certain Genes that Codify Proteins with Relevant Activities in Bio Technology A microarray with 23 different fragments of DNA from the invention that identify genes that codify proteins with relevant activities in biotechnology was prepared, in which these activities are associated to the following functions: sulfur assimilation, $CO_2$ fixation, iron oxidization, nitrogen metabolism, energetic metabolism, chemiotaxis and mobility, and biofilm formation.

Two positive controls and two negative controls were also included in the microarray. The contents of each of the positions in the microarray are detailed in Table 1 below.

TABLE 1

| Function | Position in microarray |
|---|---|
| Sulfur assimilation | A1-A3 |
| Fixation of $CO_2$ | A4-A6 |
| Iron oxidization | A7-A9 |
| Nitrogen metabolism | B2-B4 |
| Energetic metabolism | B5-B7 |
| Chemiotaxis and mobility | B8, C1-C3 |
| Biofilm formation | C4-C7 |
| Negative control | B9, C8 |
| Positive control | B1, C9 |

All the imprinted fragments were 60 nucleotides long. The DNA fragments of the invention that were chosen correspond to subfragments of 60 oligonucleotides, of the fragments shown in Table 2 which are defined in the sequence list.

TABLE 2

| Function | Position | Sequence N° |
|---|---|---|
| Sulfur assimilation | A1-A3 | 208-210 |
| Fixation of $CO_2$ | A4-A6 | 92-94 |
| Iron oxidization | A7-A9 | 193-195 |
| Nitrogen metabolism | B2-B4 | 201-203 |
| Energetic metabolism | B5-B7 | 113-115 |
| Chemiotaxis and mobility | B8, C1-C3 | 167-170 |
| Biofilm formation | C4-C7 | 2-5 |
| Negatives | B9, C8 | |
| Positives | B1, C9 | |

A company specialized in this service was entrusted with the preparation of the microarray.

Example 2

Use of the Microarrangemt for Detecting and Identifying Genes that Codify Proteins with Relevant Activities in Biotechnology The microarray obtained in example 1 was used to determine the composition of the microbiological community in two samples of bioleaching heap effluents, sample 1 (S1) and sample 2 (S2).

Total DNA present in S1 and S2 was extracted with traditional DNA extraction methods.

2 μL of DNA were taken from the samples and placed in Eppendorf tubes. The following method was followed in each case:

36 μL of $ddH_2O$ and 3.3 mL of commercial aleatory splitters of 6 nucleotides (hexamers) were added. It was brought to a boil for 5 minutes and then worked in ice.

2 μL of a mixture of nucleotides, where nucleotide dUTP is labeled with the fluorphor Cy, was added. Cy5, which presents red fluorescence, was used for S1, while Cy3 which presents green fluorescence was used for S2. After this, 4 μL of a Klenow-type polymerase and 5 μL of buffer solution appropriate for the polymerase (according to the distributor) were added; it was incubated for 4 hours at 37° C.

The reaction was stopped with 5 μL of AEDT 0.5 M pH8. The labeled DNA was recovered employing an ionic interchange column. The effluent containing the DNA was vacuum-dried.

The DNA was resuspended adding 100 μL of a buffer solution of Tris pH 7 as basic ingredient, and was submitted to 100° C. for a minute and a half to denature the DNA. Hybridizing was done on the microarray at 55° C., all night, with movement.

The following morning, each microarray was washed twice with 2×SSC, 0.1% SDS (sodium dodecyl sulfate), at 45° C.; once with 0.2×SSC 0.1% SDS at 42° C. and once with 0.2×SSC at 42° C. (For 500 of SSC 20×, 87.6 g of NaCl, 50 g of sodium citrate ($2H_2O$) and adjusted to pH 7.0)

Each microarray was placed in a box with miliQ water for 15 minutes, and was later dried by centrifugation in a Falcon Tube or something similar during one minute at 1.100 rpm.

Figure 2:
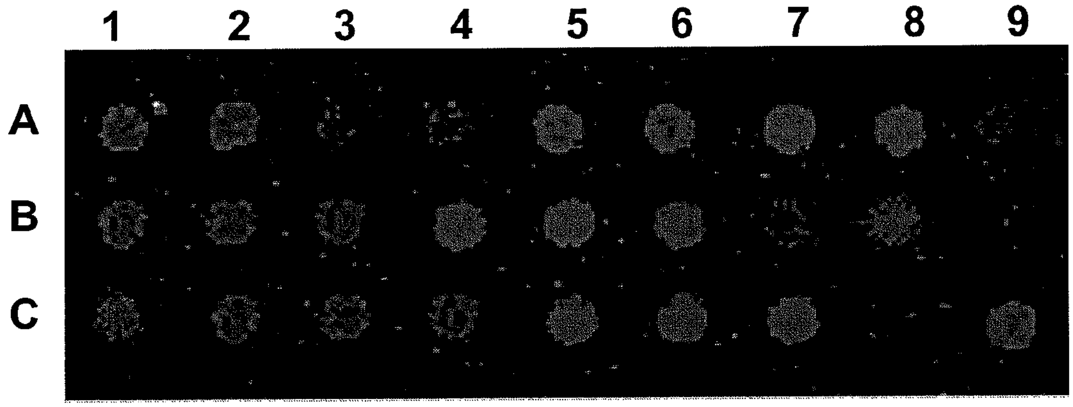
FIG. 2 corresponds to the result of hybridization of a second biomining sample with a microarray of the invention. The microarray used is the same one used for sample 1, whose contents are declared in Table 1. The fragments used in the example are contained in the sequences described in Table 2, and Table 4 sums up the positive or negative results of the hybridization. The results show the presence of genes that codify for proteins relevant for all the evaluated functions—it seems to be the case of a mixed culture. Unlike the previous sample, we observe high representation of genes for cellular movement and chemiotaxis, and for biofilm formation. Positive controls showed signs of hybridization and negative controls remained unlabeled.

Finally it was possible to observe the result of the microarrays, which are shown in FIG. 1 for S1 and in FIG. 2 for S2.

In Table 3, the positions of the different fragments in the microarray are indicated, and the result of hybridization with the DNA obtained from S1, shown in F1, is summed up. All the positive controls showed hybridization, and the negative controls remained unlabeled.

TABLE 3

| Sample 1 s(1) | | |
|---|---|---|
| Function | Position in microarray | Result |
| Sulfur assimilation | A1 | – |
| | A2 | – |
| | A3 | + |
| $CO_2$ Fixation | A4 | + |
| | A5 | + |
| | A6 | + |
| Iron oxidization | A7 | + |
| | A8 | – |
| | A9 | + |
| Nitrogen metabolism | B2 | + |
| | B3 | – |
| | B4 | – |
| Energetic metabolism | B5 | + |
| | B6 | – |
| | B7 | – |
| Chemiotaxis and mobility | B8 | – |
| | C1 | – |
| | C2 | – |
| | C3 | – |
| Biofilm formation | C4 | – |
| | C5 | – |
| | C6 | – |
| | C7 | – |

TABLE 3-continued

| Sample 1 s(1) | | |
|---|---|---|
| Function | Position in microarray | Result |
| Negatives | B9 | – |
| | C8 | – |
| Postitives | B1 | + |
| | C9 | + |

Symbols: (+): positive; (–): negative.

The results show the presence of genes that codify for proteins relevant in sulfur assimilation, $CO_2$-fixation, iron oxidization, and nitrogen-fixation functions, and key proteins in energetic metabolism. The sample does not seem to have the genes evaluated for chemiotaxis and biofilm formation.

In Table 4, the positions of the different fragments in the microarray are shown again, and the result of hybridization with DNA obtained from S2, shown in F2, is summed up. All the positive controls showed hybridization, and the negative controls remained unlabeled.

TABLE 4

| Sample 2 (S2) | | |
|---|---|---|
| Function | Position in microarray | Result |
| Sulfur assimilation | A1 | + |
| | A2 | + |
| | A3 | – |
| $CO_2$ Fixation | A4 | – |
| | A5 | + |
| | A6 | + |
| Iron oxidization | A7 | + |
| | A8 | + |
| | A9 | – |
| Nitrogen metabolism | B2 | + |
| | B3 | + |
| | B4 | + |
| Energetic metabolism | B5 | + |
| | B6 | + |
| | B7 | – |
| Chemiotaxis and mobility | B8 | + |
| | C1 | + |
| | C2 | + |
| | C3 | + |
| Biofilm formation | C4 | + |
| | C5 | + |
| | C6 | + |
| | C7 | + |
| Negatives | B9 | – |
| | C8 | – |
| Positives | B1 | + |
| | C9 | + |

Symbols: (+): positive; (–): negative.

The results show the presence of genes that codify for proteins relevant for all the functions evaluated. Apparently it is the case of a mixed culture. Unlike the previous sample, we observed a high representation of cells for cellular movement and chemiotaxis, and for biofilm formation.

The present examples are of an illustrative character and should in no way be considered as limitative of the scope of the present invention, which is defined in the accompanying claims.

The invention claimed is:

1. An array of nucleotide sequences for detection and identification of genes that encode proteins present in a microbiological sample, the array comprising the nucleotide sequence of SEQ ID NO:25 or a full-length complement thereof and a plurality of identifier polynucleotides attached to a surface of the array, wherein the identifier polynucleotides consist of polynucleotides that specifically bind to genes that correlate to a metabolic activity in a microorganism thereby detecting and identifying the genes, the plurality of identifier polynucleotides including at least one of the following:

a. a polynucleotide or complement thereof that specifically binds a biofilm formation gene selected from SEQ ID Nos:1 to 86 and their reverse complement sequences;

b. a polynucleotide or complement thereof that specifically binds a $CO_2$ fixation gene selected from SEQ ID Nos: 87 to 101 and their reverse complement sequences;

c. a polynucleotide or complement thereof that specifically binds an energetic metabolism gene selected from SEQ ID Nos:102 to 156 and their reverse complement sequences;

d. a polynucleotide or complement thereof that specifically binds a chemotaxis and mobility gene selected from SEQ ID Nos:157 to 192 and their reverse complement sequences;

e. a polynucleotide or complement thereof that specifically binds an iron oxidization gene selected from SEQ ID Nos: 193 to 197 and their reverse complement sequences;

f. a polynucleotide or complement thereof that specifically binds a nitrogen metabolism gene selected from SEQ ID Nos:198 to 203 and their reverse complement sequences;

g. a polynucleotide or complement thereof that specifically binds a sulfur assimilation gene selected from SEQ ID Nos:204 to 210 and their reverse complement sequences; or h. a polynucleotide or complement thereof that specifically binds a sulfide oxidation/reduction gene selected from SEQ ID Nos:211 to 232 and their reverse complement sequences;

where each identifier polynucleotide is present in hundreds of copies, forming dots of homogeneous composition, spatially distributed over the surface of the array.

2. The array according to claim 1, wherein the identifier polynucleotides consist essentially of 100 or less contiguous nucleotides.

3. A method for detection of genes that encode proteins present in a microbiological sample, comprising:

a) incubating a sample of labeled nucleic acid sequences, obtained from a microbiological sample, on an array of claim 1;

b) washing the array after incubation; and c) visualizing the dots of the array.

4. A method for identification of genes that encode proteins present in a microbiological sample, comprising a. extracting nucleic acid sequences from a microbiological sample;

b. incubating a sample of nucleic acid sequences obtained from the microbiological sample on an array of claim 1;

c. washing the array after incubation; and d. visualizing the dots of the array.

5. The method of claim 4, comprising fragmenting and marking a sample of nucleic acid sequences obtained from the microbiological sample using nucleotides that are labeled or susceptible to being labeled and incubating the marked sample on the array.

* * * * *

SEQUENCE LISTING

<160> NUMBER OF SEQ ID NOS: 232

<210> SEQ ID NO 1
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 1
gggaagtcat ccaggtcatc tccgtcctgg ctgtcctcaa tgcggctttc gccttttccg 60
gcaggctgcc attgtcgcgg ctgtggctgt tcagtacctg 100

<210> SEQ ID NO 2
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 2
atggccacca taagaaccag tatgcgcaca cactctacct tccaatggtc tagctggacg 60
ccttttatta tggcgctggg agatatttta gcctttcttg 100

<210> SEQ ID NO 3
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 3
gggtgcttta tcccgtcgcc atggcggcag gtgatctggt tgcgttctat tcggcgttgc 60
tggcagcgta tttcctcagg gtccatcttt tggggcactg 100

<210> SEQ ID NO 4
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 4
ctcgccgcga agcccggcat gacggggctt tggcaagtga gcgggcgcaa cgataccagc 60
tacgcgacac gggtgtcgct cgacgtgtcg tacgtgaagg 100

<210> SEQ ID NO 5
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 5
atgaatgagg gatgtacgct gcagggcggt tgccggctga tgacttccgg catgcgtatg 60
acgctgctga tgctggcatc ggatatcttt gcactggtct 100

-continued

<210> SEQ ID NO 6
<211> LENGTH: 100
<212> TYPE: DNA
<213> ORGANISM: Artificial
<220> FEATURE:
<223> OTHER INFORMATION: synthetic consensus lactobacillus lactis fragment

<400> SEQUENCE: 6
ggggatttgt ctgcgttcta tctggctctg tggatctctt acattttgag agtggacctt 60
ctcagtcggt ggattccagt tccctttacc cgaagcttcg 100

<210> SEQ ID NO 7
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 7
ttacccaacg cccgatggca cctgcrttcg ggattacatt catgtctggg atctgtgcag 60
cgcccacttg ctggctttag agcatttgct ggcygatggg 100

<210> SEQ ID NO 8
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 8
cggcataggt gaggcgcatt cgcccgaaac ccatctgctg cccaacgtac tgctggcggc 60
attgggcaga aacgacggcc tgaagatatt cggcgatgat 100

<210> SEQ ID NO 9
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 9
gatcgaggcg gtcatccatt ttgcggccgc gatcgaagtc ggggaatccg tccaggatcc 60
yctcaaatac tgggacaaca acctgaacgg cacgctccgg 100

<210> SEQ ID NO 10
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 10
ggtgcggatc gagctacagc atcctcgacc tcgtcaaggc cctctctgag atcctgaagg 60
tcacgccgga gatccgccac aaccctcccc gggccgggga 100

<210> SEQ ID NO 11
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 11

-continued acgatggccg aggtcgggct gaagacaatc gtgttctcgt cgtcggcgac ggtctacggc 60
gacccggtcc gggtgccgat caccgaagat tttccgctgt 100

<210> SEQ ID NO 12
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 12
tgatggcccg tccggtggtg ggtgacgaac cctttgcggt cttgctggcg gacgatctta 60
tgctgagcga gtctcctgtg cttgcgcaaa tggtggaaca 100

<210> SEQ ID NO 13
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 13
ggggtaaacg tgctattgcc gaccattttg atgtcgccta tgagctggaa acagaacttg 60
aaaagcgcgg taaaacagct ctactgaagg aaattcagaa 100

<210> SEQ ID NO 14
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 14
ttgtcgacgg acccgcaccg gccctgcgcc agctggtgga ggtgttcaga aaagtcaagg 60
gacctgtgat tggagtccag aaagttccgc agcaggatgt 100

<210> SEQ ID NO 15
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 15
ccccggtatt ttcagagtgc acgatcttgt ggaaaagccc gccgtcagcg aagctccgtc 60
gcgtcttgcc attgtgggac gttacattct gactcctgat 100

<210> SEQ ID NO 16
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 16
ggggaagcgc gcgatcgagg atcactttga tatctcctac gaactcgaag acgtcctccg 60
tcagaaaggc aagatggccc tcctggaaga ggtccgcaag 100

<210> SEQ ID NO 17
<211> LENGTH: 100
<212> TYPE: DNA
<213> ORGANISM: Artificial
<220> FEATURE:

<223> OTHER INFORMATION: synthetic consensus escherichia coli fragment

<400> SEQUENCE: 17
cgctttgccc tcaagcggcc ggatcttgcg gaggagttcc ggcacttcct ggccgcgacc 60
ctcgggaagg agggctcttc gtccctggga gacggacacg 100

<210> SEQ ID NO 18
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 18
gacggcgcga cgtcggtcat gaagcagatg gtcgaccagt acagctatta ccagtgctcg 60
gtcctcggcg tacagcaggt cgcgccggaa gacacggcat 100

<210> SEQ ID NO 19
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 19
tagccgacgc cgtgggccga catctrcagc gcccggcyat cgtcatcaac aaatccaccg 60
tyccagtggg cacggcgcaa aaagtgcggg aacgcatcgc 100

<210> SEQ ID NO 20
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 20
atgaaagtaa cggttgtcgg aaccggatat gtgggtctgg tcactggagc ctgccttgcc 60
caggtcggta atcaggtgct ttgcgtggat attgatgcgg 100

<210> SEQ ID NO 21
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 21
gctcggcatc gagtactacc cgatcgggcg gcccggcgcg gcgccgcgca cggcggcggg 60
cgagtccgac gccgctcgcg ccgcgcgcgc cggcgcgtga 100

<210> SEQ ID NO 22
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 22
atgaacgttt gtattgtcgg tactggctat gtaggacttg tcagcgccgc ctgctttgct 60
gaaatgggta ataccgtccg ttgcgtggac gtgaatcccg 100

<210> SEQ ID NO 23

-continued

<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 23
tagatttctc ttcaccacag attactccgc gttaaaagac gtggatattg tctttattac 60
agtcgctaca cctaccgtag aagggaagaa ctatataggc 100

<210> SEQ ID NO 24
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 24
gcgtttccgc ctacgacccg gcggcgatgg acgagacccg ccgtatctac ggcgagcggg 60
ctgacctgca actcgtcgac agcccgatgg acgccttgaa 100

<210> SEQ ID NO 25
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 25
gggatctcta cagctccctg ggaattgacg ccaaatttct gtacgaggaa ccggacggac 60
attttcccca ccaccacccg gacccgaccg ttcccgaaaa 100

<210> SEQ ID NO 26
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 26
taaaattttt tgataaagac ggattcaagc tgccggattc gcaggaagat gccataactg 60
aaatggttct gaaccagaac caccgctggg actacccgga 100

<210> SEQ ID NO 27
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 27
gaatcggtta atagtgaagc catcagagaa aggcatttga atgtggcaat tgatacagga 60
aatggtgcat catattacac aagcccggca atattgtcag 100

<210> SEQ ID NO 28
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 28
gttaaaaatc ctaaagctat aaagaagatt gttactgctg tttcaagctc aagcttagta 60

-continued gaagagtatt taagtaaata taatattcaa gttgattgga 100

<210> SEQ ID NO 29
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 29
gggttgggaa gagcataggc atgttcgtat ctggcgacgt tgccgtcgga agggatacac 60
ggatcagcgg cgatatgata gcctcttccg ttctggctgg 100

<210> SEQ ID NO 30
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 30
gtacttgctg atgcaggaaa tggtgcggca tactattcaa ctcctaaatt gcttgaaaaa 60
cttggatgct caatcactac gttaaatgca aatccggatg 100

<210> SEQ ID NO 31
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 31
gaccttcacg cctgaaatcg tcgaggccat cggtcatgcc atcggctcgg aagccgccgc 60
ccgcggccag aaggaaatct gcatcggccg cgacggccgt 100

<210> SEQ ID NO 32
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 32
tatycacrcc accgtccayc gyccctgggg cacctacacc acgctggaag arggcgaccr 60
yttcaagatc aagcggattg tcgtcaagcc cggtgaaaag 100

<210> SEQ ID NO 33
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 33
gggccgaagc atgaatcgga aacccgccgc attcttcgtc tcgcggaaaa ggaaggtctt 60
ccggcgaagg tatttgtcga accccagtcc cggaacaccc 100

<210> SEQ ID NO 34
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 34
gggtactact ggaatagcgg catgttcatg ctgaaagccg ccacgtacat ggaagaactg 60
catcgccatg caccggaaat tgcccgccag gccgaattcg 100

<210> SEQ ID NO 35
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 35
agcgtgccgt gcaggcaggg gcggaactgg ccgcacagaa ccactttgtg acgttcggca 60
tacctccggc acatccggaa actggttacg gatacattca 100

<210> SEQ ID NO 36
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 36
acgaggttat gctcctggcc gaaaaccagt cgacctacat accgctcggc accacccacc 60
ggctcgagaa ccccggcaag gtcgatcttc acatgatcga 100

<210> SEQ ID NO 37
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 37
tcttcctggg gttcgatacc catgcccttt cctggcccgc ttttgtctcg gccgtggaag 60
tcctggcggc aaacgatgtg gatgtccgga tcgccgaaaa 100

<210> SEQ ID NO 38
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 38
atgactactg ccgccaaagc cggccagttg cctgctcacg acgagcttat aaacatagca 60
cggcttgtaa gcgactttta caccgtcagc ccggaccgcc 100

<210> SEQ ID NO 39
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 39
cgaccaccag gccgtcggtc tcgaagaaaa accggacgtt ccgcgctcgt gctacgcggt 60
aaccgggctg tatttctatg acggaagtgg cagtcggatg 100

<210> SEQ ID NO 40
<211> LENGTH: 100
<212> TYPE: DNA

<213> ORGANISM: Artificial
<220> FEATURE:
<223> OTHER INFORMATION: synthetic consensus escherichia coli fragment

<400> SEQUENCE: 40
ggggcaacga tttttgccta ccacgttgcc aatcccaagg cttatggcgt ggtggagttt 60
gaccgtcagg ggattgccat tggactggaa gaaaaacctg 100

<210> SEQ ID NO 41
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 41
tcttcggcca cggacttctg gagagtctcc gccggggaac aaacctccgc aagggtgcac 60
tgattttcgg ctatccggtc cgggacccgg agcgatatgg 100

<210> SEQ ID NO 42
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 42
ccgatcacgc atgcggtgtc gaagcagctg ytgccgrtyt acgacaagcc gatgatctat 60
tacccgctgt cgacgctgat ggtggcggac attcgcgatg 100

<210> SEQ ID NO 43
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 43
ccggtatatg acaagcccat gatatattat ccgctttccg tgctgatgct ggcaggcatc 60
cgcgaggtgt gcatcatctc cacgcctgcc gacctgccgc 100

<210> SEQ ID NO 44
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 44
ggggtagcct ggttcgacac cggatttttc tgttttcccg ttgtttgccc gcgccctttc 60
ctctccttgc tttttgagga tatcattgtc atgttttcgt 100

<210> SEQ ID NO 45
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 45
acacacagga ccaaagcaac tcatcaagat cgccggcaaa cccatatcct tatggggcgt 60
tttatcactg agggatatag gcataagaga ctttgggatt 100

<210> SEQ ID NO 46
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 46
atggaggcag taatcttaca cggaggacaa ggaactcgtt taagaccatt aactcayact 60
ggycctaarc arttaataaa agttgcagga aagccaatat 100

<210> SEQ ID NO 47
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 47
ctctaatcta tatgaagatt ttacaaatgc tggatcggat ggccatctag gtttagttcc 60
agttgataat ccttcccaat tcggtatagc tgaggtcgac 100

<210> SEQ ID NO 48
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 48
atcatcgtca atattcttca caataaagcc ctgcccatyt atggygatgg ycrgcagatc 60
cgtgactggc tctatgtgga agaycaytgc cgggggatcg 100

<210> SEQ ID NO 49
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 49
ctgtcgatcc tggacgcaag gcggccgcgt ccgtcggggg cttcctaccg ggatctgatc 60
cgctttgttc cggaccgccc cggccacgac agacgatacg 100

<210> SEQ ID NO 50
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 50
aagccggccg agacgttcga gaccggactt gcgaagaccg tgcgctggta tctcgaccat 60
caggagtggg tcgacgaagt ggtgtcgggc gattaccgca 100

<210> SEQ ID NO 51
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 51

-continued

```
ataaagcgtt ttgtccacat atccacggac gaggtgtacg gttcgctgct gccccacgag     60

gcacccttca cggaaagcaa ccctctgctg cccaacagcc                          100


<210> SEQ ID NO 52
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 52

tccgggggag acctacgcca ttggcgcggg gaacccccgc accaataaag agctggtcct     60

gaccctctgc gagatcctcg accggctggc tccacgtccc                          100


<210> SEQ ID NO 53
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 53

tggagtagta aacttgttag aaatatgcag aaggtatgat acccgcctag ttcaaatctc     60

aactgacgaa gtttacggag aacaggagaa tgctacagag                          100


<210> SEQ ID NO 54
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 54

ggaaattcaa tttcaaatac gtccacatct ctacagatga ggtttayggt gaggagtgyg     60

gggatgagra ytcaccttta aaaccctctt ctccttatag                          100


<210> SEQ ID NO 55
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 55

caattttaga atacctattt acggaagtgg aaggcaaatt agagactgga tacatgtact     60

ggatcactgt agtgcgatcg aagctatact ggaaagaggc                          100


<210> SEQ ID NO 56
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 56

acacctacgg gctgccggtg ctgacgacca actgctccaa caactacggt ccctaccaat     60

tccccgaaaa actcattccg ctgatcgtgc tcaatgccgt                          100


<210> SEQ ID NO 57
<211> LENGTH: 100
<212> TYPE: DNA
<213> ORGANISM: Artificial
<220> FEATURE:
```

<223> OTHER INFORMATION: synthetic consensus escherichia coli fragment

<400> SEQUENCE: 57
ctcctggttt cgcccacggc ttttacgtgc tcagcgagtc ggcggacttt ctctacaaaa 60
ccacggagtt ttatgccccg gaagcggagc gctgcgtgat 100

<210> SEQ ID NO 58
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 58
ctttgcgcat ggcttttatg tattaagtaa ttccgctgac ttcctctata aaacaaccga 60
attttacgcc ccggaagccg agcgctgcat agtctggaat 100

<210> SEQ ID NO 59
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 59
cacattcggc cagtggttcg gactcgttct cacggcccgt gatccggagt tcctgtatgt 60
tccggaggga ttggcccacg gctttctgtc gctcgaagaa 100

<210> SEQ ID NO 60
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 60
gggcatcgaa ttcgttcagg acaatcactc ccgatccgcc cgtggcgtgc ttcgcggcct 60
gcactatcaa attcagcacg cgcaagggaa actcgtgcgt 100

<210> SEQ ID NO 61
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 61
gtaaagccta cacagcggtg ctcagtgccg caaactttct gcgcctgttc attccccggg 60
gcttcgcgca cggctacatg acactggaac cccacaccga 100

<210> SEQ ID NO 62
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 62
tattgtgtgc aatagatatg aagataacag agggtatttt gaagagcgtt acaaagcttc 60
agaatttgat cgaatactac atgttagatt tgttcaggat 100

<210> SEQ ID NO 63

<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 63
tcgccgaatt tcggccgctg ggtgggttac gagctgtcgg ccgaaaatca gagaatgctg 60
tggattccgc ccggcttcgc ccatggcttt ctggtgttgt 100

<210> SEQ ID NO 64
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 64
acggtgagcg gcaggtacag gccattctcg gtgataccgc actcatcctg cgtaccgcct 60
gggtctatag cgcccacggc agcaacttcg tcaaaaccat 100

<210> SEQ ID NO 65
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 65
gggatggtgc cgttcattgt gcagaggctg cccgtaaaca ttctgcccgg ctcatccata 60
tttccacgga ttttgtattt gatgggagtc aggcgacccc 100

<210> SEQ ID NO 66
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 66
tggcggttgc ggagaccggc ggcgactggc tgacgtttcg caccacgtgg gtgttcgccg 60
cacgcggcaa gaacttcctg cgaacgatgc ttcgtcttgc 100

<210> SEQ ID NO 67
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 67
ggcaacatgc atcttgtcca ctacagcacc gacttcgtct ttaacggacg caaggaaacg 60
ccgtatacag aagatgacga aaccgccccg cagagcatct 100

<210> SEQ ID NO 68
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 68
gcgcgaggca gcaacttcct gctgacgatg acgcgcctca tgcgcgaacg gccggaactc 60
aagatcgtcg ccgatcagat gggcgccccg acctggtgtc 100

<210> SEQ ID NO 69
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 69
gggagatggt gcagtcctgc gcggatctcg gtattcccta cctgacgctt ttcgctttca 60
gcaccgagaa ctggcgacgt ccagccattg aagttcgttt 100

<210> SEQ ID NO 70
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 70
gggagatggt tcagtcgtgt gtagacttga atattcccca tcttactctc tttgcgttta 60
gcactgaaaa ttggcggcgg cctcctttgg aggtgcgtct 100

<210> SEQ ID NO 71
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 71
cgggcgtcga atatctgacg ctcttcgcgt tcagctccga gaactggcgc cggccgaacg 60
acgaagtgtc gttcctgatg cgcctgttca tcaccgcgct 100

<210> SEQ ID NO 72
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 72
gactctttac gcgttttcgc aggaaaactg gggacggccc aaaaaagaag tggggttcct 60
ctttgatctg ctggtcagct ttctgcgtga tgaactgccc 100

<210> SEQ ID NO 73
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 73
atgagtatag cccataagat aggagatatc gcctcaggcg tttacgaaca ggctttaatg 60
gaagagataa ggaaagccga tgtcccactt catctaggga 100

<210> SEQ ID NO 74
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 74
gggttatcta caaatgaggg gcatgtgagg ggaaaagata aattagaaga ggtccttgac 60
tgggctatgg aggttggaat caaaatagtt acagtatacg 100

<210> SEQ ID NO 75
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 75
tggcctayac cgaaatgtac tttacrccga ccytgtggcc ggatttcaga gaagaggatt 60
ttcggcaggc gatcgaagat ttccaggaga gaagacgccg 100

<210> SEQ ID NO 76
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 76
cgatttgtta tggaggcagg caagaaatat tggatgctat aaggaaaatc atgaatgatt 60
ataaattagg tataatagat tcaaaatcca tagatgagtc 100

<210> SEQ ID NO 77
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 77
gctatcaata ataacaacat atattaagag aggtatacaa gatttactag aagatcccat 60
cgtagataag tatgaagtta aagtaagtgc aataggtaaa 100

<210> SEQ ID NO 78
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 78
atacgaataa gtaatttcct tttatggcat atagcgtatt cagaactctt ttttgtagac 60
acatattggc cagactttag aaagatagac ttatggagag 100

<210> SEQ ID NO 79
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 79
ttgttgactg gtgcatggaa ctagacataa gaatcgtaac gttttatgca ttctcgacag 60
agaactttcg taggagtccc gaagaggtcg atttcctctt 100

<210> SEQ ID NO 80
<211> LENGTH: 100
<212> TYPE: DNA

<213> ORGANISM: Artificial
<220> FEATURE:
<223> OTHER INFORMATION: synthetic consensus escherichia coli fragment

<400> SEQUENCE: 80
tcaatgctcc cagagtatct aagagagacc attaagataa cagaggaaac gactaaaaac 60
ttctctaatt accatatgaa cctcgccata gggtacggag 100

<210> SEQ ID NO 81
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 81
gacaacagcc gcctcacgtt cacggtcgcc gcgaattacg gcggacgctg ggacgtcgtg 60
caggccgtca agaaactcgt cgcgtcgggc gaaccggtga 100

<210> SEQ ID NO 82
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 82
gggagatatc gtctacgtgc cgcaaacgac cgtcagcagc tggaatcaag ccatactgct 60
cctgttgccg tccctgcagg ccatcaacca gttgctcaac 100

<210> SEQ ID NO 83
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 83
tttgggtggc acagtgaatc taccagaggc cgatttgcgt ggggcttata tcgtacaaaa 60
cggtaagaaa ttgccggtca acttccatca gctactcaga 100

<210> SEQ ID NO 84
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 84
cgcgctcacg gcgggaggcg gcattctcga taccgatgcg aatccgcgtc aggtgtacgt 60
gttgcgcgat ctgcaggaca agccgaacac accggacatc 100

<210> SEQ ID NO 85
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 85
cagtatcaga ttctccatca cggccaagcc ttgctcaccg gcaagatcga ycagccygcc 60
gttggacccg agttgcggct gatgctgact gcggtgaagt 100

<210> SEQ ID NO 86
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 86
gtgactgatc acactgaaaa tatgcatccg tccgagaacg tcgatctgca acggcggcca 60
tcaattgcca acaactctga acgtatggga gatgaaggag 100

<210> SEQ ID NO 87
<211> LENGTH: 100
<212> TYPE: DNA
<213> ORGANISM: Artificial
<220> FEATURE:
<223> OTHER INFORMATION: synthetic consensus methanosarcina acetivorans fragment

<400> SEQUENCE: 87
tggaggaact ggcccgcctt gaaaaggcgc cgatcatggc ccayatggcc atgtccggyt 60
ggctctggca caaggacggg atgtcggtgc gttcctggac 100

<210> SEQ ID NO 88
<211> LENGTH: 100
<212> TYPE: DNA
<213> ORGANISM: Artificial
<220> FEATURE:
<223> OTHER INFORMATION: synthetic consensus methanosarcina acetivorans fragment

<400> SEQUENCE: 88
agtcctggga cgcctggtcc cagaagatcc ctcttgaaaa ataccgaaag ggccacaagg 60
ctctggatcg ggcactcaca gcctttgcta cctatgtgtg 100

<210> SEQ ID NO 89
<211> LENGTH: 100
<212> TYPE: DNA
<213> ORGANISM: Artificial
<220> FEATURE:
<223> OTHER INFORMATION: synthetic consensus methanosarcina acetivorans fragment

<400> SEQUENCE: 89
aaggcaaggc tgttctcact gaggcggcca agcactcccc cgaactcaag atygccatgg 60
aaacgtggaa agagatcaag ttcgarttcg atacggtcga 100

<210> SEQ ID NO 90
<211> LENGTH: 100
<212> TYPE: DNA
<213> ORGANISM: Artificial
<220> FEATURE:
<223> OTHER INFORMATION: synthetic consensus methanosarcina acetivorans fragment

<400> SEQUENCE: 90
ccccgagtac gtgcctttgg actctgatat cttagcctgt ttcaaaatta cgccacaacc 60
aggggtggat cgtgaagaag ccgccgccgc ggtagccgcc 100

<210> SEQ ID NO 91
<211> LENGTH: 100
<212> TYPE: DNA
<213> ORGANISM: Artificial
<220> FEATURE:

<223> OTHER INFORMATION: synthetic consensus methanosarcina acetivorans
fragment

<400> SEQUENCE: 91
atggaccagt cctcacgtta tgccgatctc tctctgcgcg aagaagatct gatcgccggt 60
ggcaagcaca tactggttgc ctacaaaatg aaacccaaag 100

<210> SEQ ID NO 92
<211> LENGTH: 100
<212> TYPE: DNA
<213> ORGANISM: Artificial
<220> FEATURE:
<223> OTHER INFORMATION: synthetic consensus methanosarcina acetivorans
fragment

<400> SEQUENCE: 92
ggtcaggcca agctgttctc gatgaacatc accgcygacg accaytacga ratgtgcgcc 60
cgcgccgact acgcgctcga agtcttcggc cccgacgccg 100

<210> SEQ ID NO 93
<211> LENGTH: 100
<212> TYPE: DNA
<213> ORGANISM: Artificial
<220> FEATURE:
<223> OTHER INFORMATION: synthetic consensus methanosarcina acetivorans
fragment

<400> SEQUENCE: 93
ggcaactact ggtatatgtg gaagttgccc atgttcggcg aaacggacgt ggacaccatt 60
ctgaaagaag cggaagcctg ccataaggcg aatccccata 100

<210> SEQ ID NO 94
<211> LENGTH: 100
<212> TYPE: DNA
<213> ORGANISM: Artificial
<220> FEATURE:
<223> OTHER INFORMATION: synthetic consensus methanosarcina acetivorans
fragment

<400> SEQUENCE: 94
cgcatcaaca tactactggt acatgtggaa actgcccatg ttcggcgagc agtcagtgga 60
caccgttatt gccgaactgg aggcatgcca tcgcgcccac 100

<210> SEQ ID NO 95
<211> LENGTH: 100
<212> TYPE: DNA
<213> ORGANISM: Artificial
<220> FEATURE:
<223> OTHER INFORMATION: synthetic consensus methanosarcina acetivorans
fragment

<400> SEQUENCE: 95
gggctcagat tcagtacatt gtcgctcagg gttggaaccc tgcagtagag catgtcgagc 60
ccagtcgctc gttcacgcat tactggtaca tgtggaagct 100

<210> SEQ ID NO 96
<211> LENGTH: 100
<212> TYPE: DNA
<213> ORGANISM: Artificial
<220> FEATURE:
<223> OTHER INFORMATION: synthetic consensus methanosarcina acetivorans
fragment

<400> SEQUENCE: 96
gcggacatcc gcaagcaggt cgagtacctg gtctccaagg gctggaaccc ggccatcgag 60
cacaccgagc ccgagcacct gatggactcg tactggtaca 100

<210> SEQ ID NO 97
<211> LENGTH: 100
<212> TYPE: DNA
<213> ORGANISM: Artificial
<220> FEATURE:
<223> OTHER INFORMATION: synthetic consensus methanosarcina acetivorans fragment

<400> SEQUENCE: 97
gggactytac agygaratyg ccgtyacccc rctgtttgar accattcacg atctggagcg 60
tatggatrct gtcatgtcca cgctgctcga taacccggtt 100

<210> SEQ ID NO 98
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 98
aggaagtgat gctcggctat tcggacagca acaaggacgg cggcttcctc acgtcgaact 60
gggagctcta tcgcgcggaa ctggcgctcg tcgatctgtt 100

<210> SEQ ID NO 99
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 99
caggaggtca tgctcggcta ttccgactcg tgcaaggacg gcggcatcct cgcgtcgaac 60
tggaacctct atcaggcgca gctttcgatc atcgcactga 100

<210> SEQ ID NO 100
<211> LENGTH: 100
<212> TYPE: DNA
<213> ORGANISM: Artificial
<220> FEATURE:
<223> OTHER INFORMATION: synthetic consensus synechococcus sp. fragment

<400> SEQUENCE: 100
gggcgctgtc gatgtaacca attacgtcga tctgctggtg ggtgtggtgc cggtggtcaa 60
cttggagtgg attcagaaga ttcaccgtga caatgcccag 100

<210> SEQ ID NO 101
<211> LENGTH: 100
<212> TYPE: DNA
<213> ORGANISM: Artificial
<220> FEATURE:
<223> OTHER INFORMATION: synthetic consensus synechococcus sp. fragment

<400> SEQUENCE: 101
gccgaagccg aaggcaattt ctcgttcagc cacttcggcc cgcaggccaa ccatttcgac 60
aagctcgcgg aactgttcaa gacctatggc gagaccggcg 100

<210> SEQ ID NO 102
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 102
gtcgacagtc atatttatgc gggttatcgg gtaccrcctt tctatgaytc catgatcggy 60
aaaatcatcg ccttcggggg tgaccgcgag gaagccaaca 100

<210> SEQ ID NO 103
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 103
ggggcatgcg gatcgtccat caggaaagtg aattcgaaaa cgctctccat gcagcccaga 60
cggaagcttt tcaggccttc ggatcgaaag aggtttacat 100

<210> SEQ ID NO 104
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 104
ggtggccgaa atttcggcca agggatataa cccgcatgtg aagcttgacg agtaccgcac 60
ccgcgagact ccgcgcatgc ctgatttcag gcctgtgctg 100

<210> SEQ ID NO 105
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 105
ctgtcgttcc cggaagtcag ggagcgatct cgtctgaaga ggaagccatc acgctctccc 60
gagaaatcgg ctatcccctg atcatcaagg cttccgcagg 100

<210> SEQ ID NO 106
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 106
cgagacagtg ttctccgatg taagcagaga rttytayttc cttgarttaa ayaaragryt 60
acaagttgaa catccaataa cagagaccat attcagaata 100

<210> SEQ ID NO 107
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 107
gggaggtgga gcaggagtgg gtattataaa ggttgataat cctagtgaac tagctgaggc 60
ttttgaaaga agcaaaagat tagcgtactc tgcctttggc 100

-continued

<210> SEQ ID NO 108
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 108
cgtcgggytt cacgttcatc ggcccgcgcc ccgacaacat ccgcctgatg ggcgacaaag 60
tcgcggccaa gcaggccatg atcgacgcca aggtgccctg 100

<210> SEQ ID NO 109
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 109
tattatcggc ggtctggcgc gcttcaatgg acagccgatc gtctggatgg gacatcagaa 60
gggccgygac acyaaggaaa aratycagcg yaaytttggg 100

<210> SEQ ID NO 110
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 110
gggcccagga aaggccgacg gctctcgact atatccagcg gctctgcacc cagttcatcg 60
aaattcacgg tgaccgttcc ttcagggatg acccttccat 100

<210> SEQ ID NO 111
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 111
ggcgaccgcg cgttcgcgga cgaccagtcg atcgtcggcg gccttgctcg cttcaacggc 60
catgcgtgca tggtgatcgg ccatcagaag ggccgcgata 100

<210> SEQ ID NO 112
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 112
cgatcctgac cttcatcgac accccgggcg cctatcccgg gatcggtgca gaggagcgcg 60
gccagtcgga agcgatcgcc cgcaacctct atgtcatggc 100

<210> SEQ ID NO 113
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 113
ccagggctat atgatcaaat cccccatggt cgggactttt tatcgcgcat cctctccgga 60
atctccaccc ttcgtggaag aaggcagcat ggtgaaggcc 100

<210> SEQ ID NO 114
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 114
atggatatcc aattcattcg tcgccttgcc gaattacttg aaaaaagcgc tattgacgaa 60
attgaagttg tggaaggtga aagtaaggtg cgtattaccc 100

<210> SEQ ID NO 115
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 115
gaatccggca tctccgaact ggaagtcacc gaaggcgaag gtaaggtgcg catcgtcaag 60
aacgcgccgc cggtctatgt gcagccgtcg gccggcttcg 100

<210> SEQ ID NO 116
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 116
catctccgaa ctggaagtca ccgaaggcga aggtaaggtg cgcatcgtca agaacgcgcc 60
gccggtctat gtgcagccgt cggccggctt cgcgccgcag 100

<210> SEQ ID NO 117
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 117
atggatctca gaaaactgaa aaagctcatt gatctggtcg aggcctccgg catcgccgaa 60
ctcgaaatca ccgaaggcga ggaaaaggtc cgcatcgcca 100

<210> SEQ ID NO 118
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 118
ctggattttt tcctggatgc agaaccgcgc ctggaaattg ccaaggaata tgtccccgtt 60
gatcccctgc gyttcaarga tcagaagcgc tayaaggagc 100

<210> SEQ ID NO 119
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 119
gggttcctga gggattgtgg atcaagtgtt ccctctgtcg acaaattgtc taccggaaag 60
aagtcgaaaa agcaggaaaa gtctgtccga aatgcaatta 100

<210> SEQ ID NO 120
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 120
cccgagggcc tgtgggtcaa gtgcccgtcg tgcgaggccg tgctgtaccg caacgacgtc 60
gatgcgaatc agcacgtgtg cccgaagtgc gatcaccaca 100

<210> SEQ ID NO 121
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 121
gggtctcgaa gatgccgtca aggtcggaga gtgtcggatc gagggaatcc cgaccgttct 60
tggtctcttc tcctttcatt tcatgggagg atctatgggg 100

<210> SEQ ID NO 122
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 122
cccagttgtc gcgcaaccgg ctgcccttcg tttcggtgct gaccgacccg acgatgggtg 60
gcgtttccgc cagcttcgcg atgctcggcg acctgatcgt 100

<210> SEQ ID NO 123
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 123
ggaaccgaac tttgcgccag gtctggaggg tgtggctgca acccagtcca gcatttccaa 60
catcgatggc gctgccggcc tgctgagtta ccgtggtttt 100

<210> SEQ ID NO 124
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 124
atgaccccgt ctgatgttaa agccacgcta tcgttcagcg ataattcgcc gagcgtcgaa 60
ctgccgatct acaagggtac gatgggcccc gacgtgatcg 100

<210> SEQ ID NO 125
<211> LENGTH: 100

<212> TYPE: DNA
<213> ORGANISM: Artificial
<220> FEATURE:
<223> OTHER INFORMATION: synthetic consensus escherichia coli fragment

<400> SEQUENCE: 125
ctctttgaaa ttgcagtraa actygaggaa cttggtgtaa argarttcgg tggcaaaggg 60
aatatatcca atacagatta ttattccggc atagttttca 100

<210> SEQ ID NO 126
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 126
taagaagtat cttgacattg ctgaaagact tgaaaagtta ggagtagaaa cattctcagg 60
taaaggagtc tatccaaata cagacttcta ctcagggatt 100

<210> SEQ ID NO 127
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 127
tatagaagaa aggagggtaa taagccaaga attccagagc cctcagatag ttttgcaaaa 60
agctttcttt tagcgagttt cgctagggaa cctactacag 100

<210> SEQ ID NO 128
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 128
acgcatcaac ctttgcctca ttagttgtag cctctacttt ttcagattta tattcttcta 60
tagtagctgg gatatcagca ttgaaagggc ctttgcacgg 100

<210> SEQ ID NO 129
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 129
catcggaray aaagttcaag tggaayaagg atacggacag rgaygttgca gcagaaatga 60
tcggcaggat gtcagcgata accgtgaacg tgtacaggca 100

<210> SEQ ID NO 130
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 130
acgaaggcct gctgtactac cggggctacc cgatcgacca actcgcctac cagtcggact 60
tcatggaagt cagctacctg ctgctgcacg gcgaactgcc 100

-continued

<210> SEQ ID NO 131
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 131
gtgaccatgg cgcatgttca gattccggct caggggaagc ccatcaccca ggtggacggg 60
gtgctgcggg tgcccgatca accgattatt cccttcatcg 100

<210> SEQ ID NO 132
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 132
gggtcaggat atctggaacg cctccgtgcg cgtgttcgat gccgctgtcg aaaaagctta 60
caagggcaag aaaaaagtgg tctggttcga agtgtatgcc 100

<210> SEQ ID NO 133
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 133
cccgtgggca aggggttccg cagtctcaac gtgaccatgc gccagactct cgacctgtat 60
gcctgcatcc ggcccatacg gtatttcgaa ggcatcgaat 100

<210> SEQ ID NO 134
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 134
agagtggaaa gaaattcttg taggggacaa agcactgaaa gagaaaaatg atcgtttccc 60
ggaagaatca caggaggcaa taaaacaata ccgtgtactg 100

<210> SEQ ID NO 135
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 135
gggagtgatg atgctccgct ggatcggtga aaatgccgcc gcggacaaga tcgagaaggg 60
catgaacaag gttctggccg aggccaagac cctgacctac 100

<210> SEQ ID NO 136
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 136
acaaaagaaa gtcacccagg atatagcgag atacctaggt atcacacctc taggaacaaa 60
ggaatatact gacacacttg tgcaaataat ggactccttc 100

<210> SEQ ID NO 137
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 137
gtgggtagaa gttctagcag gagataaggc agaaaagcta accggaaata gatttcctaa 60
agagtcagag gaattgatag agaagtatag agtcttatta 100

<210> SEQ ID NO 138
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 138
ggcatatatt caagtgaagg aggatggaac ccttcaggtt ccagatagag taactatagg 60
atatatagag ggcgatggaa taggacctga tatatcaaag 100

<210> SEQ ID NO 139
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 139
ggggatggta taggccccga tatcacgaag accacgataa atgtaataaa tgctgccctt 60
gaggtcgcct atggtggaaa gagatcaata gaatggcaca 100

<210> SEQ ID NO 140
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 140
ctggatggag gtctttgccg gcgagaaagc cgtcaaggtc tacggcggcg accagtggtt 60
gcccgaagaa accgtttccg ccgtcaggga ctacgtgatt 100

<210> SEQ ID NO 141
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 141
caacggtcga gcgtatgcgc caagaggttc aggaagaagt ggcagatgcg gtcacttttg 60
ccgaacagag cgccgcaccg gatatggagg atgcctggaa 100

<210> SEQ ID NO 142
<211> LENGTH: 100
<212> TYPE: DNA

-continued

<213> ORGANISM: Artificial
<220> FEATURE:
<223> OTHER INFORMATION: synthetic consensus mycobacterium tuberculosis
fragment

<400> SEQUENCE: 142
gtccgggatg caagaccgat ttttcttacc tgcgcctgtc gccagccggc aaggtgcgca 60
aaccccccat cgacgtcgcc cccgccgaca cgagcgactt 100

<210> SEQ ID NO 143
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 143
gggatttgtg catctctatg taggtgaaga ggctgtagct gtaggggtta tgagtacgct 60
aagagatgat gactatataa ctagtacgca tagaggacat 100

<210> SEQ ID NO 144
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 144
cagatctgga aatccgattc tggtggaggc gagaagctac aggatggggc cgcattcaac 60
atcggacgat cccagcaagt accgcaagaa cgaggtgcag 100

<210> SEQ ID NO 145
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 145
gtgtttacgt tgatggaaac gacttcataa aaacttacaa tgccgtaaag gaggctgttg 60
aatacgcaag atcaggaaat ccgatacttg tcgaggccag 100

<210> SEQ ID NO 146
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 146
gtggttcccg ctactccgca ggatgcctac tggcagttgc gccaagccat ccgcagcgat 60
gatcccgtga tagttctcga gcatgagttg ctctatttcg 100

<210> SEQ ID NO 147
<211> LENGTH: 100
<212> TYPE: DNA
<213> ORGANISM: Artificial
<220> FEATURE:
<223> OTHER INFORMATION: synthetic consensus mycobacterium tuberculosis
fragment

<400> SEQUENCE: 147
cggcgatgct gggtctgcgc ccggtggtcg aaatcatgac catcaatttt gctttgtttg 60
ccattgacgc catcatcaac atggccgcca agatcccgtt 100

<210> SEQ ID NO 148
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 148
agatgcaaag ggactgatgc tttcctccat cgaggacaac aatcctgtcc tgatctttga 60
acaccgctgg ctcatgaaaa ggaaaggggc cgttccggaa 100

<210> SEQ ID NO 149
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 149
gcggctctac aacggcccgt tcgacggcca ccacgaacgg ccggtgacgc cgtggagcaa 60
gcatccggcg agcctcgtgc ccgacggcta ctacacggtg 100

<210> SEQ ID NO 150
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 150
tatttttgat aaaaaggtta atttcgcctg tgccggaatt gtaggttcat cttttccctc 60
tgcacttgga gcagccctgg catcgaaact cgatggtaaa 100

<210> SEQ ID NO 151
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 151
atgactcaga tgacaatggt aaaagcactg aacagcggtt taaataatgc catggagaga 60
gatgattcca tcatacttct gggagaagat gttggtaccg 100

<210> SEQ ID NO 152
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 152
accacggagg gtcttctggc aacgtacgga gattggcggg tccgggacac gcccatctcc 60
gagaacagct ttaccggcct cggcgtggga gcggccatgg 100

<210> SEQ ID NO 153
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 153
atacacccat tactgaacaa acatttatgg gcattagcgt tggcgctgct tcctctggct 60
tacacccagt tgtttcatta atgttcgtag actttctagg 100

<210> SEQ ID NO 154
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 154
atgaacatgg ttcaggcact gaacagtgca atggatctca agatgtccga ggatgacagc 60
gtaataatac tcggagagga cgtaggcagg gatggaggtg 100

<210> SEQ ID NO 155
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 155
catttacacc gcaatggatc aaataataaa tcagatggca aagataaggt acagatctgg 60
tggagattac acagtgccgc ttgtccttag gactcctgtt 100

<210> SEQ ID NO 156
<211> LENGTH: 100
<212> TYPE: DNA
<213> ORGANISM: Artificial
<220> FEATURE:
<223> OTHER INFORMATION: synthetic consensus mycobacterium tuberculosis fragment

<400> SEQUENCE: 156
cttcggctat aacatttctg tgcactggtg cctgaaagcc gccgaaatcc tcgacaagca 60
gtacggcatc tcggccgagg tcgtcgacct ttattcgctc 100

<210> SEQ ID NO 157
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 157
gataaaagcg tggctttggg gtataccgta gtggacccgg ccaccgtcat tgccacccag 60
ttgcaccaga ttctccaaag ccatggtgcg gacttactgg 100

<210> SEQ ID NO 158
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 158
gggaaaaaca ggagtttgcc gatcatcagt tttgaccgga gatgggaaga tgtgtttctc 60
aagcaggccg cacagacacc gcagggatcg cccctcgccc 100

<210> SEQ ID NO 159
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 159
gggatggctc agcacgacat gagcttcgcc gcggcgggca agaactacac gctgctcacg 60
atcggcgacg gcctcgtcgc gcagatcccg tcgctcgtga 100

<210> SEQ ID NO 160
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 160
tgtgacttcc atgttcatgc tttccccgct tgaattttcc atttttcctt cgcttctgct 60
ggttaccacg ctgctgcgtc ttgctcttaa cgtggcaagt 100

<210> SEQ ID NO 161
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 161
gggaaatggc gcgccggcgg atgatggcag ccattcctaa agccgatgtc attgtgacca 60
acccaaccca ctatgccgtt gccctgcgtt ataaagaagg 100

<210> SEQ ID NO 162
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 162
agccgcgagg tcggttcgct gttttttctg atctcggccc ttctcctgtt cggcgcgacc 60
ggacacggca tcatggtcag tcttgaagac cagatggcca 100

<210> SEQ ID NO 163
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 163
gcaccatgct gcacaccgca ttctcgttcg accgcgcagc cgcgttcgat acgaaccgga 60
tgctgtcgca cgcgggcacg ctgagcctcg aagggctcta 100

-continued

<210> SEQ ID NO 164
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 164
caagctggcg ctcatgctgc tgcccatcat gctgtttctc gcgcttgtgg cgtatgtggt 60
catccgtctg caggtgggca aactgtgggc gcccaaagtt 100

<210> SEQ ID NO 165
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 165
ctggccaagg tcggtctgct cggcggcgtt gccgcatggc tcgtctggtc gaacgtcgag 60
gcgatcgtga gcctgagcct cgaagcaccc acggccgcga 100

<210> SEQ ID NO 166
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 166
atgccaaacg tatttacacg ttcaggagac ctgcgcaaga aagctatgca atggtggtct 60
gataaaagtc agcaacacaa gttatttatt ctcataggcg 100

<210> SEQ ID NO 167
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 167
gggaaagtgg cttctccgcc gctggggccg aacaatacct cggaaacgcg ctactccaag 60
aaaaaacaga tcgcccatta tcatgtcagc cggacggacc 100

<210> SEQ ID NO 168
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 168
aacagcgcgt tctcggccgc ggccgatccg ttcgcgaacc tgccgtggtg gcgccagccg 60
gacatgatcg aactcggcaa ggacatcgcg aaatggctgg 100

<210> SEQ ID NO 169
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 169
gggcaagatt ctgtactacc ccaaagacga acagtcgctt gacggcatga cctccaccca 60

-continued gctggaacac aagctgacca tgcagcagaa tttcgaacgc 100

<210> SEQ ID NO 170
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 170
ccccttgggc cccaaggatg gaacgcagac gaaatattcg aagaagaagg atatcgaaca 60
ctacgacgtg agccatacca tgagccacat cgttctcccc 100

<210> SEQ ID NO 171
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 171
tcaccgtcgt cgaccagaac ggcaatctgc tgtccgacgc cggcaaggcc ccgcgcgtca 60
acggcatgga tccgagccag atcaaatacg tgcaagagct 100

<210> SEQ ID NO 172
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 172
atggctgatc tgacaggccg tacaggcacg ttgaatagtg ggttggatta tgccgcagtc 60
tttctcctgg gcgtcggccc agatgatgct tctttgatta 100

<210> SEQ ID NO 173
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 173
gggaaggagc aggcggacaa gattctcgag atgatgaacg atcaggaagg gagcagtctc 60
cagtcgctga agtggatgga tcccaaatcc atcgccaacc 100

<210> SEQ ID NO 174
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 174
ctgaaggctt gaacaagagc gcgctcctgc tgatgtcgat cggcgaggaa gaggccgcgc 60
aggtattcaa attcctcgcg ccgcgcgaag tgcagaagat 100

<210> SEQ ID NO 175
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 175
cttatcagca acctgccggc aggtgtgcgc cccgaagtgc tgatgcgcct tgccaaactg 60
gaagcagtgc ccgaagacat gctgatggaa gtggacaagg 100

<210> SEQ ID NO 176
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 176
tcacgagtct cggcgtcagc cggatcgaga agacggcgaa ccttttgaac gagatggacc 60
gctccacctc ggaggggatc ctcgacttca tcagccagaa 100

<210> SEQ ID NO 177
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 177
caacttcatg agcggcgaaa acgaggcaat cgcgatggag tacctgaaaa gctacgaccc 60
cgacatggcg cagaagatca tggacgagat gttcgtgttc 100

<210> SEQ ID NO 178
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 178
atggtacagg atattctttc tcaggatgaa gtggatgccc tatttaaggg catgtcagat 60
ggtgatgtcg aaatgcacgc tgaacctgag cctgatccgg 100

<210> SEQ ID NO 179
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 179
tggaaaaccg gagatgtctt ttccctggac cggtatgtca gcgagcctgt ggaggttcgc 60
gtggagggca tcctccgctt tctggggagg cccggaattt 100

<210> SEQ ID NO 180
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 180
gcctcgaaat catcaacgat cgcttcgcgc gcctcttgcg gatcggcatc ttcaacttca 60
tgcggcgcac ggcggaaatc tccgtgagcc aggtgaaggt 100

<210> SEQ ID NO 181
<211> LENGTH: 100

-continued

<212> TYPE: DNA
<213> ORGANISM: Artificial
<220> FEATURE:
<223> OTHER INFORMATION: synthetic consensus escherichia coli fragment

<400> SEQUENCE: 181
ctgccattgt gccgcccagt gacgttgttg tggtcatcac ctttgaggtg gaactggaat 60
cggccatcgg ttcgctggtt atgtgtctgc cgtatgccac 100

<210> SEQ ID NO 182
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 182
ccccgtctcc acggagatga tcaagtttgg ggagttcatc aagaaaatcc ctctcccgtc 60
gaacatcaac attcttcgcc tcgaaccgat gaaacgcaac 100

<210> SEQ ID NO 183
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 183
atgcgcatac ggaaaattca acggccagta caccctgcgc gtcgaaaagc tgttgtcgac 60
cagcgcggtc gaaccgaaaa caggagagca gcatgtctga 100

<210> SEQ ID NO 184
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 184
gatcgcgcag ggcgaagtgg tggtcgtcaa cgacaagttc ggcatccggc tcaccgacat 60
catcacgccg tccgaacgca tccggaagct gaaccgatga 100

<210> SEQ ID NO 185
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 185
gatcgcgcag ggcgaagtgg tggtcgtcaa cgacaagttc ggcatccggc tcaccgacat 60
catcacgccg tccgaacgca tccggaagct gaaccgatga 100

<210> SEQ ID NO 186
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 186
gaagacacca cgcaaacgat cgccgaggac gattgggccg cggccatggc cgagcaggcc 60
gcgccggccg ccgcccccgc ccccgagatc ttcaaggaat 100

<210> SEQ ID NO 187
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 187
gggagatgga aattcccatt catgccctgg ttcgtaccgc cgacggaatg cctgccttcg 60
gtattgttgc tgcggtaatg ggcgtggtaa ataccatggg 100

<210> SEQ ID NO 188
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 188
catcatcggc aacggcatca agacgatcaa ggcgacgctg cgcgtgctgc ccacgctgtt 60
caagggctcg aagtacaaca aggacatcta catggagctg 100

<210> SEQ ID NO 189
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 189
cctttctcgt cggcaacaac aacaaggtga tcaaggcgac gctgaaggcc ttgccgaccg 60
tgctcaaagg ctcgaagtac acgcgcgcgc tttacatgga 100

<210> SEQ ID NO 190
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 190
gggacgtgcc aacgctgttc gccaggtgct ggttcagaat ggtctggatg aaagtaaaat 60
actgagagta gtcggcatgg gatcggcggt gttgtacgtg 100

<210> SEQ ID NO 191
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 191
aggtgaagct gatggcrgcc atcgaggcga atccgacgct gcgccagttc aagcagcaga 60
tccgcatcga ttcgacgctg atggggctgc gcatcgaaat 100

<210> SEQ ID NO 192
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 192
ggccaatgtt caacctcgcg agcgccgagt tgcagcccta taccaaggtc atcctgcacg 60
agatcgcaca ggtcctcaac gacgtcgaaa accgcatcag 100

<210> SEQ ID NO 193
<211> LENGTH: 100
<212> TYPE: DNA
<213> ORGANISM: Artificial
<220> FEATURE:
<223> OTHER INFORMATION: synthetic consensus acidithiobacillus
ferrooxidans fragment

<400> SEQUENCE: 193
atgatggaaa ccgggtgaat cccatcatgc agcccgtggc ggaaaagctg accaaccggc 60
aaatgcggga ggtggcggct tatctgtccg gtctgcattg 100

<210> SEQ ID NO 194
<211> LENGTH: 100
<212> TYPE: DNA
<213> ORGANISM: Artificial
<220> FEATURE:
<223> OTHER INFORMATION: synthetic consensus acidithiobacillus
ferrooxidans fragment

<400> SEQUENCE: 194
gggtatcggc acttacgaag cctatatttt tgggcaggat aaggccaact ggctctactt 60
cgaggcggac ggatacacca acgcggacgg tattggtgta 100

<210> SEQ ID NO 195
<211> LENGTH: 100
<212> TYPE: DNA
<213> ORGANISM: Artificial
<220> FEATURE:
<223> OTHER INFORMATION: synthetic consensus acidithiobacillus
ferrooxidans fragment

<400> SEQUENCE: 195
aagatggtgg ccatggtatc tgtcgtgttt attggtatgg gtgcgatgcc ttttgacaca 60
attgcttatg gagcggcaag cgcaccgaac agcaagattg 100

<210> SEQ ID NO 196
<211> LENGTH: 100
<212> TYPE: DNA
<213> ORGANISM: Artificial
<220> FEATURE:
<223> OTHER INFORMATION: synthetic consensus acidithiobacillus
ferrooxidans fragment

<400> SEQUENCE: 196
gggacacgtt tacgatccca aactcgtggc cgaagggaaa aagctgtact tcggtggtct 60
gcccgacaaa cacatgccgg cctgcatggc ctgccatggc 100

<210> SEQ ID NO 197
<211> LENGTH: 100
<212> TYPE: DNA
<213> ORGANISM: Artificial
<220> FEATURE:
<223> OTHER INFORMATION: synthetic consensus acidithiobacillus
ferrooxidans fragment

<400> SEQUENCE: 197
gcccaacatc aaacccatcg tcgcgggtac cggattcagt cctgttccca agggtggaaa 60
gttcggrtay acggayttya cctggcatcc gacrgccggc 100

<210> SEQ ID NO 198
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 198
atgaaagtac gtgcacaatt tgctctcgtt tttaatctag ataagtgcat cggttgtcat 60
acatgctcgg tgacctgcaa aaatacctgg accaaccgtc 100

<210> SEQ ID NO 199
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 199
aactgggaag acgacctcgg cggcgagttc aagtcgcgca gccgcgacaa gctgttcgag 60
gccgtgcaaa aggagatgta ctcgacgttc gagaacacct 100

<210> SEQ ID NO 200
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 200
atgaaagtca gagcgcaatt cgccttcgtc ttcaacctgg acaagtgcat cggatgtcac 60
acctgctcgg tgacctgcaa gaacgtctgg accaaccgca 100

<210> SEQ ID NO 201
<211> LENGTH: 100
<212> TYPE: DNA
<213> ORGANISM: Artificial
<220> FEATURE:
<223> OTHER INFORMATION: synthetic consensus azotobacter vinelandii
fragment

<400> SEQUENCE: 201
gcggaagtga tcggtgacga cctgaacgcc ttcatcaaaa cctccaagga aaagggcagc 60
gtaccagaag aatatgatgt gcctttcgcc catactccgg 100

<210> SEQ ID NO 202
<211> LENGTH: 100
<212> TYPE: DNA
<213> ORGANISM: Artificial
<220> FEATURE:
<223> OTHER INFORMATION: synthetic consensus azotobacter vinelandii
fragment

<400> SEQUENCE: 202
aaaaaggatc ggttccccag gaatacgatg ttccctttgc ccataccccg gccttcgtgg 60
ggtcgcacat caccggctac gacaatgcgc tgaagggaat 100

<210> SEQ ID NO 203
<211> LENGTH: 100
<212> TYPE: DNA
<213> ORGANISM: Artificial
<220> FEATURE:
<223> OTHER INFORMATION: synthetic consensus synechococcus sp. fragment

<400> SEQUENCE: 203
ggggcctgcg gagacgatac gagaaacatc accacctgcc cgatgagcgg tctggatccc 60
catcccgaaa acaatttttc ggatctggtc gaagaagcga 100

<210> SEQ ID NO 204
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 204
caggtgttgg ccatagccga agccgtgctc attacccagc gtgaccacgg agaccgaagc 60
aatcgaagcc acgcccgcct caaatacacg gtagaccgta 100

<210> SEQ ID NO 205
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 205
tagagaaata tcagttgtat gttggtggag gaatgggcga gaataatggt tatccgacat 60
tttctgcttt agcacttcct ttgggtacag taagtgagga 100

<210> SEQ ID NO 206
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 206
ctggatatcc ctcaccatct ctaaaactga ctacgagaca agctattcaa tttcaccacg 60
taaagaaaag ggatttacct aaccttataa gagaggtcgc 100

<210> SEQ ID NO 207
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 207
tagatgctat agttaggata caacaagaat ggggtgatag aaagaatcgt cattgggcta 60
ggttgaaata tttagtatat aaaatgggag tagaatggat 100

<210> SEQ ID NO 208
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 208
ggggttgcct cgacatttct ggcggatcgt gtcgccatcg gccggcctgt acccatattt 60
atcgaaccca atgccgaatt ccggctaccc gaagattccg 100

<210> SEQ ID NO 209
<211> LENGTH: 100
<212> TYPE: DNA

<213> ORGANISM: Artificial
<220> FEATURE:
<223> OTHER INFORMATION: synthetic consensus escherichia coli fragment

<400> SEQUENCE: 209
aacggcgtgc acggggtgac aagggccgca actggttgtt ctttggcgag cacacgcagc 60
caccgatttc tactatcgcg acgaacttgc tagctagcta 100

<210> SEQ ID NO 210
<211> LENGTH: 100
<212> TYPE: DNA
<213> ORGANISM: Artificial
<220> FEATURE:
<223> OTHER INFORMATION: synthetic consensus escherichia coli fragment

<400> SEQUENCE: 210
tcgcggctcg tcgcgaacct gcggctcaac gagccgggtg cggcgaagga cacgcgctgc 60
gtgtcgctgt cgrcggacgg cgcggcgatc gaatacgaaa 100

<210> SEQ ID NO 211
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 211
aggtactggg cagtgggcat atggaaacgt tgtaggacct ctatttaata actctaagct 60
tccaaaactt gaaataacat acataagtgc atccccagag 100

<210> SEQ ID NO 212
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 212
ctccgcaagg cttatgcttg atcatgaata tcactgatat tgatggtcca gatgcatatc 60
cagcatctgc tcccttaatg gaaatatcta atggaacatg 100

<210> SEQ ID NO 213
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 213
gtgggaaaga tggcaaataa acaagtcgta gataacctaa ctagaaagga atacttgttc 60
cctataaggt tcgcagtagg ttggatgttc ttcgatggag 100

<210> SEQ ID NO 214
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 214

-continued tattcttagt tataggactt ttgacaagat tagctgcctt tggtgcagct gtaatggcta 60
ttggtatggc tccagcttac tggttaggtt caacgtgcga 100

<210> SEQ ID NO 215
<211> LENGTH: 100
<212> TYPE: DNA
<213> ORGANISM: Artificial
<220> FEATURE:
<223> OTHER INFORMATION: synthetic consensus paracoccus denitrificans fragment

<400> SEQUENCE: 215
ccccggatca tcaggagaaa gatcatgggt agtgcaacga gcgtaaacgg cagtacattt 60
tcagtggaca gaggatggcg cctggcggcg atagggctgc 100

<210> SEQ ID NO 216
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 216
atatctggga cctgcgcggt tccggcctga ccaacatgca cggctccacc ggtgacatcg 60
ttctgctggg taccaccact ccccagctgg aagagatttt 100

<210> SEQ ID NO 217
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 217
ggcccttcgc tgcggacctc gatgtcctgc gtcggcgccg cacgctgcga gcattcctgt 60
tatgacgagg cccatgcgct gcgcactgtc atcaacaaca 100

<210> SEQ ID NO 218
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 218
tgtgcgaaat cccgctggcc gttgcttcct gccccaccgc cgctgttcgt cccaccaagg 60
ttgaactgga cggcaaaaag gtgaacagca tcgccatcaa 100

<210> SEQ ID NO 219
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 219
tcaagctgtc gacctcctgc tgcgaaatca actgcggcgg ccaggctgac atcgccatca 60
tcgtccagca caccaagccg ccgaagatca accacgatct 100

-continued

<210> SEQ ID NO 220
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 220
aggctatctg gtcgacctgt cgcagtggaa cgaagacatc gccaagtaca tggccgtcga 60
agaaaaagtc gaactgaccg acagccactg ggaagtcgtc 100

<210> SEQ ID NO 221
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 221
tcaaggacga actccttgcc cccggattcc ggatctccgg actgggtcag ttggtcgaga 60
tgggcattca gtacgatcgt ctcgtgacgt tcggtgatta 100

<210> SEQ ID NO 222
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 222
ttcaccgacg acgggatcta ccagttgatg aagggcatcg acaccaaggg catcgaggtc 60
aaggacttct cgaagaccta tcgtgcgctg gaaggctacg 100

<210> SEQ ID NO 223
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 223
gggtatttac accttcatgg gatatctgat gctcttccac gagatagggc tggactatac 60
cctgtccacc tacgcatcag aaggcggcaa cttcggtctg 100

<210> SEQ ID NO 224
<211> LENGTH: 100
<212> TYPE: DNA
<213> ORGANISM: Artificial
<220> FEATURE:
<223> OTHER INFORMATION: synthetic consensus acidianus ambivalens fragment

<400> SEQUENCE: 224
gtggcggctg ctgaatttga cgttccggaa ctgaaggacg acatcgaagt tcccaagata 60
agggaaggct cgatggcgca cgccaagtcg ttcctcgcgc 100

<210> SEQ ID NO 225
<211> LENGTH: 100
<212> TYPE: DNA
<213> ORGANISM: Artificial
<220> FEATURE:

<223> OTHER INFORMATION: synthetic consensus acidianus ambivalens
      fragment

<400> SEQUENCE: 225
atggctgtca cgacgaacaa agcagcaaag accgaaggca tgacgtggcg tcgctacaag     60
gatggcgagt cggaagcgaa catccgttcg gctcaggacc                          100

<210> SEQ ID NO 226
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 226
gggattcgtg tacagaatca tggattgggc aaaatcgccc gttcctttcc gcatcccgac     60
aacgagtgga cagcagaaat ctttgccctg gatcaagccc                          100

<210> SEQ ID NO 227
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 227
ccagaagggc gtcatctacc ggatggccaa ggaagtcgtg ctgttcgaat ccctgttcaa     60
gtccaacaag tggatctggg tgttcggctg gctcttccat                          100

<210> SEQ ID NO 228
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 228
ttctcgcggg ctacgtgcat cgccgcggcg cgggggcgcg cggctggatc gtcccgtttc     60
tgaatcaggt acgcgcgcac aaggcgcgcg tttccgctta                          100

<210> SEQ ID NO 229
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 229
ccccgatagc gagatctcga agcgtttgcg cgaactgccc accaagcagg tgcgtgccga     60
cctcaagctc aataccggcg ttcgctatca cggaatctaa                          100

<210> SEQ ID NO 230
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 230

-continued

```
aactctacgg cagcgcgatg ctggcgccga tgttcatcat catgtccttc gcctacggtc     60

tcgcgatcta cctgatggtg ctggttgctg cctacgcctg                           100


<210> SEQ ID NO 231
<211> LENGTH: 100
<212> TYPE: DNA
<213> ORGANISM: Artificial
<220> FEATURE:
<223> OTHER INFORMATION: synthetic consensus acidianus ambivalens
      fragment

<400> SEQUENCE: 231

acgacgcgct gtccccggaa gacgagctcc gcctgcacgt actcttcaac accgagctgc     60

gggcggttcg catcgacgag tcgagcatga ccctatgggc                           100


<210> SEQ ID NO 232
<211> LENGTH: 100
<212> TYPE: DNA
<213> ORGANISM: Artificial
<220> FEATURE:
<223> OTHER INFORMATION: synthetic consensus allochromatium vinosum
      fragment

<400> SEQUENCE: 232

accacgctca ccgagatgac gggcgaaacg atcaagacga tcatggaaga cgtcgccgac     60

aatctgttca acgccgaccc gtactaccag cagggcggcg                           100
```